United States Patent [19]
Sato

[11] Patent Number: 6,087,502
[45] Date of Patent: *Jul. 11, 2000

[54] ACRIDINIUM COMPOUND HAVING A PLURALITY OF LUMINESCENT GROUPS AND BINDING GROUPS, AND CONJUGATE THEREOF

[75] Inventor: Naofumi Sato, Tokyo, Japan

[73] Assignee: Mochida Pharmaceuticals Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/690,732

[22] Filed: Jul. 31, 1996

[30] Foreign Application Priority Data

Aug. 1, 1995 [JP] Japan .................................. 7-196573

[51] Int. Cl.$^7$ ................................................. C07D 219/00
[52] U.S. Cl. .............................................................. 546/104
[58] Field of Search ............................................... 546/104

[56] References Cited

U.S. PATENT DOCUMENTS

| | | | |
|---|---|---|---|
| 4,946,958 | 8/1990 | Campbell et al. | 546/104 |
| 5,227,489 | 7/1993 | Law et al. | 546/104 |
| 5,281,712 | 1/1994 | McCapra et al. | 546/104 |
| 5,438,139 | 8/1995 | Sato et al. | 546/104 |
| 5,468,646 | 11/1995 | Mattingly et al. | 546/104 |
| 5,523,212 | 6/1996 | Akhauautafti et al. | 546/102 |
| 5,594,112 | 1/1997 | Sato et al. | 530/391.3 |

FOREIGN PATENT DOCUMENTS

| | | |
|---|---|---|
| 0082636 | 6/1983 | European Pat. Off. . |
| 0257541 | 3/1988 | European Pat. Off. . |
| 0263657 | 4/1988 | European Pat. Off. . |
| 0273115 | 7/1988 | European Pat. Off. . |
| 0322926 | 7/1989 | European Pat. Off. . |
| 0324202 | 7/1989 | European Pat. Off. . |
| 0330050 | 8/1989 | European Pat. Off. . |
| 0353971 | 2/1990 | European Pat. Off. . |
| 0609885 | 8/1994 | European Pat. Off. . |
| 2588259 | 4/1987 | France . |
| 5-255263 | 10/1993 | Japan . |
| 5-255264 | 10/1993 | Japan . |
| 6-9566 | 1/1994 | Japan . |
| 6-158039 | 6/1994 | Japan . |
| 1461877 | 1/1977 | United Kingdom . |

OTHER PUBLICATIONS

Sato et al Chem. Abstr. vol. 126 entry 84748, 89241, 1996.
Sato et al Tetrahedron Lett. vol. 37, No. 47 pp. 8519–8522, Nov. 1996.
Rapaport et al, J. Amer. Chem. Soc., vol. 94, No. 9, pp. 3153–3159 (1972).

Primary Examiner—Mukund J. Shah
Assistant Examiner—Bruck Kifle
Attorney, Agent, or Firm—Birch, Stewart, Kolasch & Birch, LLP

[57] ABSTRACT

Acridinium compounds and their conjugates exhibiting high chemiluminescence yield are provided. Such compounds may be used to enable a highly sensitive specific binding assay. The acridinium compounds are represented by formula (I):

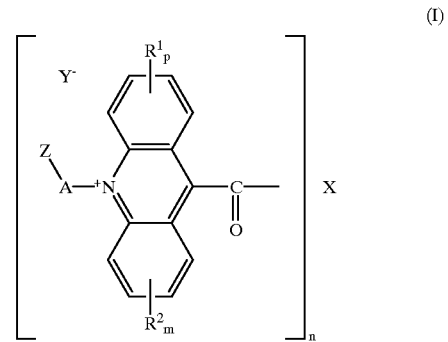

wherein A is a linker; Z is a binding group; Y is a counter ion; $R^1$ and $R^2$ are independently a substituent; p and m are independently an integer of from 0 to 4; n is an integer of from 2 to 5; and X is an organic intervening moiety with a functionality of at least $\underline{n}$, having an aryloxy group or an arylsulfonamide group through which X binds to carbonyl carbon bonded to 9-position of the acridinium ring.

8 Claims, 11 Drawing Sheets

MDAC-1

MDAC-2

MDAC-3

MDAC-4

MDAC-5

MDAC-6

MDAC-7

MDAC-8

MDAC-9

MDAC-10

MDAC-11

MDAC-12

MDAC-13

MDAC-14

MDAC-15

MDAC-16

MDAC-17

MDAC-18

MDAC-19

MDAC-20

MDAC-21

MDAC-22

MDAC-23

MDAC-24

MAC-1

SAC-1

ACRIDINIUM COMPOUND HAVING A PLURALITY OF LUMINESCENT GROUPS AND BINDING GROUPS, AND CONJUGATE THEREOF

BACKGROUND OF THE INVENTION

This invention relates to an acridinium compound which may be used as a chemiluminescent label in a specific binding assay, and a conjugate thereof, and more specifically, to an acridinium compound which exhibits a high chemiluminescence yield enabling a high sensitive specific binding assay, and a conjugate thereof.

Acridinium compounds are useful for a chemiluminescent label since their luminescence efficiency is higher than other chemiluminescent compounds such as luminol. A chemiluminescent label is not only required to have a high luminescence efficiency but also required to have a functional group that enables the labeling procedure, and a stability of practical level upon use in the specific binding assay whether the compound is used as it is or after forming a conjugate with the specific binding substance.

An acridinium compound used for such chemiluminescent label should contain a functional group which has a covalent bonding activity with the so called specific binding substance so that the functional group may serve a binding group upon binding with the specific binding substance. A specific binding substance is a substance that constitutes a specific binding pair such as an antigen and an antibody and other immunological pairs; a lectin and a sugar chain; a ligand and a receptor; an enzyme and a substrate; and a target nucleic acid and its complementary nucleic acid. The acridinium compound used for the chemiluminescent label should also contain a moiety which serve a leaving group upon formation of the dioxetane on the carbon atom at 9-position in the acridinium ring. The moiety of the leaving group is typically phenoxy group which is bonded to the carbon atom at 9-position of the acridinium ring with the intervening carbonyl group. There are two types of compounds which differ in the location of the functional group for the labeling purpose. In one type of the compounds, the functional group for the labeling purpose is located on the part of the phenoxy group which is bonded to the carbon atom at 9-position of the acridinium ring with the intervening carbonyl group. In another type of the compounds, the functional group for the labeling purpose is located on the part of the nitrogen atom at 10-position of the acridinium ring.

The compound having the functional group for the labeling purpose on the part of the leaving group is significantly limited in the choice of modification on the benzene ring of the phenoxy group. In addition, synthesis of the compound is rather difficult since the functional group for the labeling inherently has a high reactivity. In contrast, the compound having the functional group for the labeling purpose on the side of the nitrogen atom at 10-position of the acridinium ring has no functional group for the labeling on the side of the leaving group, and therefore, modification of the leaving group is not so difficult.

European Patent Application Laid-Open EP 82636A (Patent family: U.S. Pat. No. 4,946,958) proposes an acridinium ester compound wherein the functional group for the labeling is an active derivative of a carboxylic acid which is present as a substituent on the phenoxy group of the leaving group in the ester moiety. In this type of the acridinium ester, the acridinium ring is highly electron attractive and the carbonyl group is susceptible for nucleophilic attack, and the compound is unstable and easily hydrolyzed. The stability of the compound is insufficient for practical use.

European Patent Application Laid-Open EP 324202A (Patent family: U.S. Pat. No. 5,521,103) proposes an acridinium ester compound and an acridinium acylsulfonamide compound wherein carboxymethyl group for the labeling purpose is present on the nitrogen atom at 10-position of the acridinium ring. In the compounds of the European Patent Application Laid-Open EP 324202A, the carboxymethyl group on the nitrogen at 10-position is a rather large sized substituent, and steric repulsion is generated between the hydrogen atoms on the carbon atoms at 4- and 5-positions of the acridinium ring and the carboxymethyl group. It is estimated that the planar structure of the acridinium ring is no longer retained, and ester bond of such compound is more stable compared to the acridinium compounds retaining its planar structure wherein methyl group is present on the nitrogen atom at 10-position. Such stability is advantageous for use of the compound in the specific binding assay wherein the specific binding reaction such as hybridization of oligonucleotide or an immunoreaction is utilized for the assay.

European Patent Application Laid-Open EP 263657A (Patent family: U.S. Pat. No. 4,745,181) proposes an acridinium ester compound wherein the phenoxy group of the leaving group in the ester moiety has the functional group for the labeling purpose, and 2 substituents are introduced at ortho position of the phenoxy group in the ester moiety for the purpose of improving the stability of the acridinium compound in the solution.

With regard to improvement in the stability of the acridinium compound in the solution, European Patent Application Laid-Open EP 322926A (Patent family: U.S. Pat. No. 5,281,712) proposes an acridinium ester compound wherein 2 electron donor groups are introduced at ortho position and an electron attraction group is introduced at meta or para position of the phenoxy group in the ester moiety; and Japanese Patent Application Laid-Open No. 6(1994)-9566 proposes an acridinium ester compound wherein substituents are introduced at para position of the acridinium ring and at ortho position of the phenoxy group in the ester moiety.

European Patent Application Laid-Open EP 609885A (Patent family: U.S. Pat. No. 5,438,139) proposes an acridinium ester compound of higher stability and higher luminescence efficiency having the functional group for the labeling on the side of the nitrogen atom at 10-position of the acridinium ring. In this compound, carboxymethyl group is present on the nitrogen atom at 10-position of the acridinium ring, and in addition, at least one substituent is present at ortho position of the phenoxy group.

European Patent Application Laid-Open EP 257541A and, EP 273115A (Patent family: U.S. Pat. No. 5,468,646) propose an acridinium acylsulfonamide compounds which are estimated to be more stable than the acridinium ester compound.

European Patent Application Laid-Open EP 330050A, proposes an acridinium compound wherein solubility in water of the compound is improved by incorporating a hetero atom in the molecule.

European Patent Application Laid-Open EP 353971A (Patent family: U.S. Pat. No. 5,227,489) proposes an acridinium ester compound wherein an ionizable group is incorporated at para position of the phenoxy group to improve hydrophilicity, and hence, stability in liposomes; and Japanese Patent Application Laid-Open No. 5(1993)-255264 proposes an acridinium ester compound wherein sulfonium ion is introduced in the molecule to improve solubility of the compound in water.

Japanese Patent Application Laid-Open No. 5(1993)-255263 proposes an acridinium compound which has a structure different from either of the acridinium phenylester compounds and the acylsulfonamide compounds. In this compound, hydrazino group is present in the moiety of the leaving group to reduce blank value and enable use in the assay of high sensitivity.

Japanese Patent Application Laid-Open No. 6(1994)-158039 proposes an acridinium ester compound wherein 2 acridinium rings are present in one molecule.

In spite of the proposals as described above, the compound of these proposals suffered from various insufficiencies.

The acridinium ester of European Patent Application Laid-Open EP 82636A was unstable when stored in the state of solution, and use of this compound for the chemiluminescent label in a specific binding assay was not practical.

In the acridinium esters of European Patent Application Laid-Open EP 263657A and European Patent Application Laid-Open EP 322926A wherein improvement in stability has been attempted, the functional group having the binding activity with the proteins was present on the part of the phenoxy group in the leaving group, and modification of the phenoxy group had been greatly limited. Synthesis of such compounds were also difficult since the functional group with the binding activity inherently had a high reactivity.

The acridinium acylsulfonamide compounds described in European Patent Application Laid-Open EP 257541A, EP 273115A and European Patent Application Laid-Open EP 330050A also had the functional group involved in the binding on the part of the leaving group, and suffered from structural limitation and difficulty in the synthesis as in the case of the above-mentioned acridinium ester compounds. In addition, these acridinium acylsulfonamide compounds were inferior to the acridinium ester compounds in luminescence efficiency.

The acridinium compounds described in Japanese Patent Application Laid-Open Nos. 5(1993)-255263, 5(1993)-255264, 6(1994)-9566 and 6(1994)-158039 also had the functional group involved in the binding on the part of the leaving group, and suffered from the above-described structural limitation and difficulty in the synthesis.

The acridinium compounds of European Patent Application Laid-Open EP 353971A was designed for use with liposomes, and the compounds could not be used for the chemiluminescent label unless additionally processed.

In contrast to the acridinium compounds as described above, the acridinium compounds described in European Patent Application Laid-Open EP 324202A and EP 609885A had the functional group (binding group) for the labeling provided with an activity to bind to proteins and the like on the part of the nitrogen atom at 10-position of the acridinium ring, and the presence of such functional group also resulted in improved stability. In these compounds, modification on the part of the leaving group was also considerably easy owing to the absence of the functional group for the labeling purpose on the part of the leaving group. Furthermore, synthesis of these compounds were quite convenient since introduction of the functional group for the labeling purpose on the nitrogen atom at 10-position of the acridinium ring could be effected at the final stage of the synthesis. These compounds, therefore, were quite useful.

Furthermore, in the acridinium ester described in European Patent Application Laid-Open EP 609885A stability of the ester bond and luminescence efficiency of the acridinium are improved by the presence of the substituent on the phenoxy group of the leaving group in the ester moiety. Further increase in the luminescence efficiency is desired to enable the specific binding assay of higher sensitivity.

SUMMARY OF THE INVENTION

In view of the above described situation, an object of the present invention is to provide an acridinium compound which exhibits a high luminescence efficiency; which can be conveniently used in the labeling of proteins, nucleic acids, and the like; whose high luminescence efficiency is retained even after the labeling procedure; which has an excellent stability; and which can be synthesized by a simple procedure. Another object of the present invention is to provide a conjugate of such an acridinium compound with a specific binding substance.

To achieve the objects as described above, the inventors of the present invention made an extensive study, and found that an acridinium ester compound which has a functional group for the purpose of labeling introduced on the part of the nitrogen atom at 10-position of the acridine ring, and which has 2 or more acridinium ring in one molecule exhibits a high luminescence efficiency as well as an excellent stability. The present invention has been completed on the bases of such finding.

According to first aspect of the present invention, there is provided a compound represented by the formula

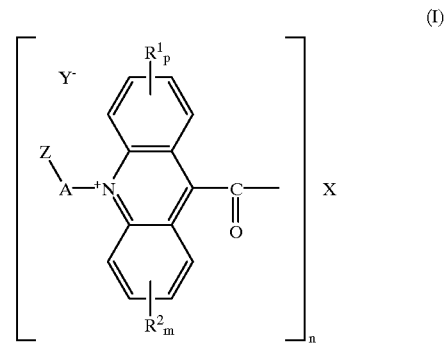

(I)

wherein A is a linker; Z is a binding group; Y is a counter ion; $R^1$ and $R^2$ are independently a substituent; p and m are independently an integer of from 0 to 4; n is an integer of from 2 to 5; and X is an organic intervening group with a valence of at least $\underline{n}$, having an aryloxy moiety or an arylsulfonamide group through which X binds to carbonyl carbon bonded to 9-position of the acridinium ring.

According to second aspect of the present invention, there is provided a conjugate of the acridinium compound of the first aspect of the present invention with a specific binding substance.

According to third aspect of the present invention, there is provided a process for producing the acridinium compound of the first aspect of the present invention, comprising the steps of reacting 1 mole of a compound having the group X with at least 2 moles of a compound having the group represented by formula (XII):

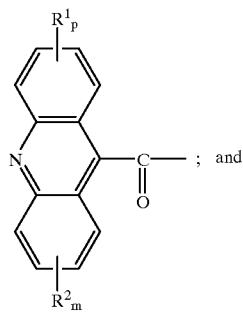

(XII)

reacting a compound having the group Z—A— with the nitrogen atom at 10-position in the acridine ring of the resulting compound.

DETAILED DESCRIPTION OF THE INVENTION

Figure 1:
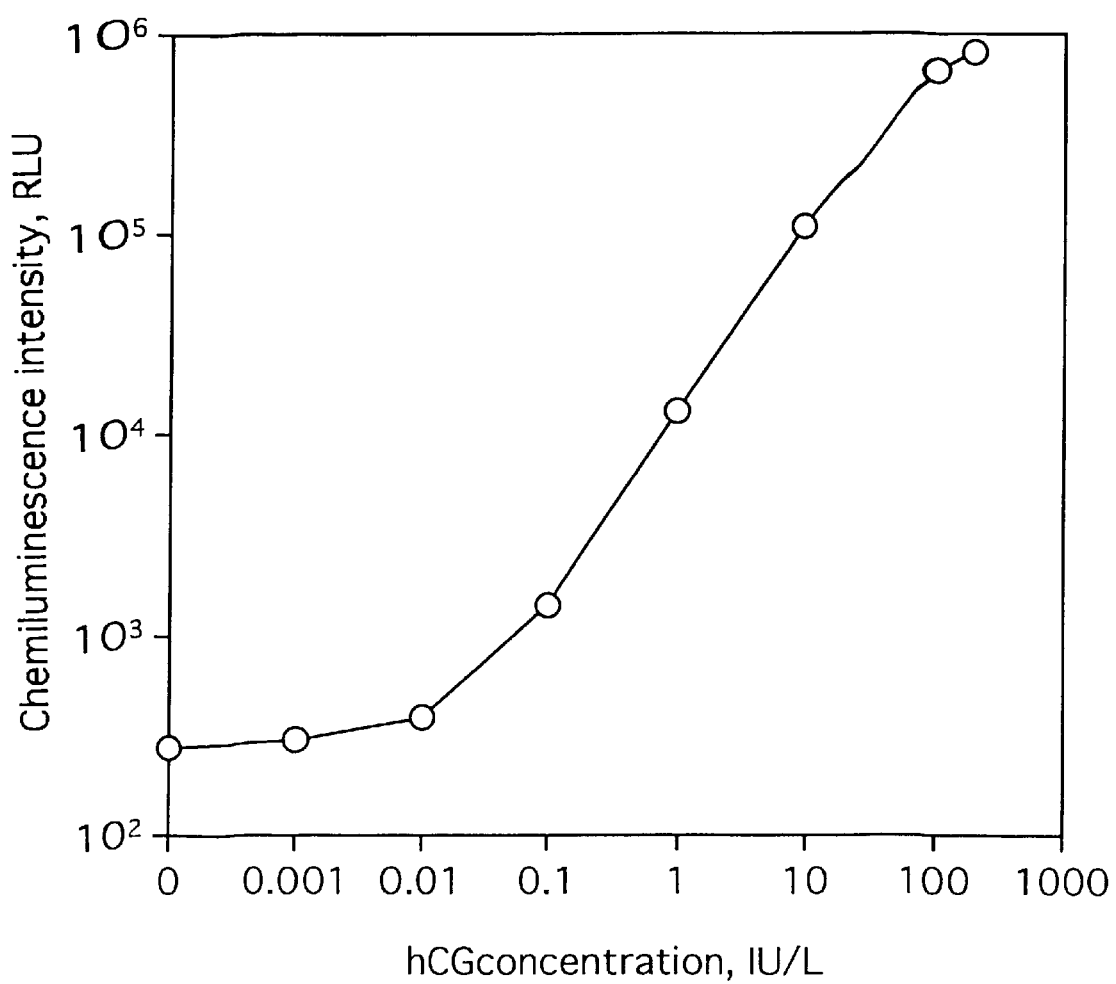
FIG. 1 is a graph showing the standard curve depicted by measuring chemiluminescence intensity in relation to hCG concentration.

Next, the acridinium compound of the present invention (hereinafter sometimes referred to as "the compound of the present invention") and the conjugate of the acridinium compound of the present invention with a specific binding substance are described.

In formula (I) representing the compound of the present invention, A is a linker which is a divalent organic group linking the functional group (binding group) Z for the labeling as will be described below and the nitrogen atom in the acridinium ring. The linker A itself does not serve a functional group for labeling the specific binding substance. The linker A is typically an alkylene group, an aralkylene group, or an arylene group having 1 to 10 carbon atoms, and preferably, an alkylene group or an arylene group having 1 to 10 carbon atoms. Typical alkylene groups having 1 to 10 carbon atoms include methylene group, butylene groups and octylene group, and typical arylene groups include phenylene group and naphthylene group. One or more carbon atoms constituting A may be replaced with a hetero atom, which may typically be nitrogen, oxygen, sulfur or the like. The linker A may also have one or more substituents, which may typically be an alkyl, an aryl, an alkylene, an alkoxy, an aryloxy, a halogen, protected amino, protected hydroxy, oxo, thio, imino, or mercapto group.

More preferably, A is an alkylene group having 1 to 4 carbon atoms wherein one or more carbon atoms may be replaced with a hetero atom, or substituted with a substituent.

Most preferably, A is an alkylene group having 1 to 4 carbon atoms.

Z is a binding group, namely, a functional group for the purpose of labeling which can bind to a specific binding substance such as an antibody, an antigen, a hapten, a lectin, a sugar chain, a glycoprotein, a receptor, a ligand, avidin, biotin, an enzyme, a substrate, an inhibitor, a target nucleic acid, a complementary nucleic acid or the like. Typical examples of Z include carboxyl group, an alkoxycarbonyl group, carbamoyl group, an aryloxycarbonyl group, hydroxyl group, cyano group, carboxyimide group, isocyanate group, isothiocyanate group, an azide group, sulfonic acid group, sulfonamido group, a sulfonyl halide group, a halogenated carbonyl group, N-succinimidyloxycarbonyl group, N-phthalimidyloxycarbonyl group, and maleimide group.

Preferably, Z is selected from carboxyl group, and halogenated carbonyl group, N-succinimidyloxycarbonyl group, or N-phthalimidyloxycarbonyl group which are reactive derivatives of the carboxyl group.

More preferably, Z is carboxyl group. Use of N-succinimidyloxycarbonyl group for Z is also advantageous in view of convenient labeling procedure.

$R^1$ and $R^2$, which may be either the same or different, are substituents on carbon atoms at 1- to 8-position of the acridinium ring, and may be selected from the group consisting of an alkyl group, an aryl group, an alkoxy group, a phenoxy group, nitro group, cyano group, an acyl group and a halogen atom. Typical alkyl groups are methyl, ethyl and butyl groups; and typical aryl groups are phenyl and naphthyl groups. Typical alkoxy groups are methoxy, ethoxy, conbutoxy; and typical acyl groups are acetyl, propionyl, and benzoyl groups. Typical halogen atoms include chlorine, bromine and fluorine.

Preferably, $R^1$ and $R^2$ are independently a lower alkyl group or a lower alkoxy group having 1 to 4 carbon atoms, or a halogen atom.

In the compound of the present invention, both $R^1$ and $R^2$ are free from binding activity with the specific binding substance.

Y is a counter ion, which may typically be $CH_3SO_4^-$, $FSO_3^-$, $CF_3SO_3^-$, $C_4F_9SO_3^-$, $CF_3COO^-$, a halide ion, $BF_4^-$, $PF_6^-$, or a group represented by the following formula:

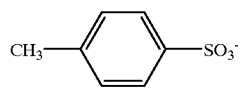

(5)

p and m are independently an integer of from 0 to 4, and preferably, 0 or 1. When p or m is 0, hydrogen atom, and not the substituent, is bonded to the carbon atom.

n is an integer of at least 2, typically an integer of from 2 to 5, preferably 2 or 3, and more preferably, 2.

X is the moiety that leaves the acridinium ring as a leaving group upon formation of the dioxetane on the carbon at 9-position of the acridinium ring, and is an organic intervening moiety with a valence of at least $\underline{n}$, X has an aryloxy group or an arylsulfonamide group, and X binds to carbonyl carbon bonded to the 9-position of the acridinium ring through the aryloxy group or the arylsulfonamide group. X has no functional group for the labeling purpose.

Typical examples of X are the groups represented by the following formulae (II), (III), (IV), (V), (VI), (VII), (VIII), (IX), (X), and (XI):

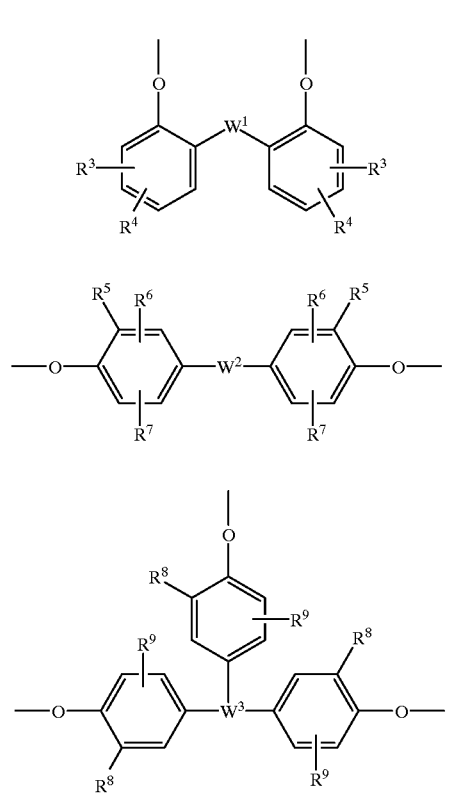

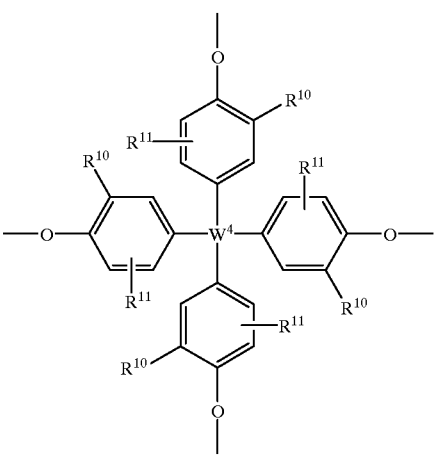

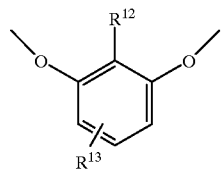

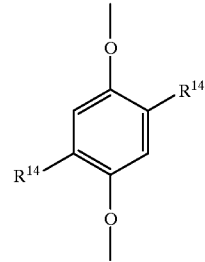

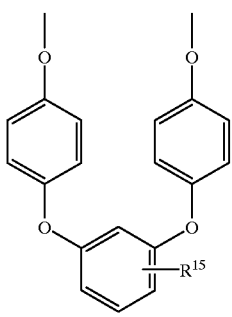

-continued (IX)

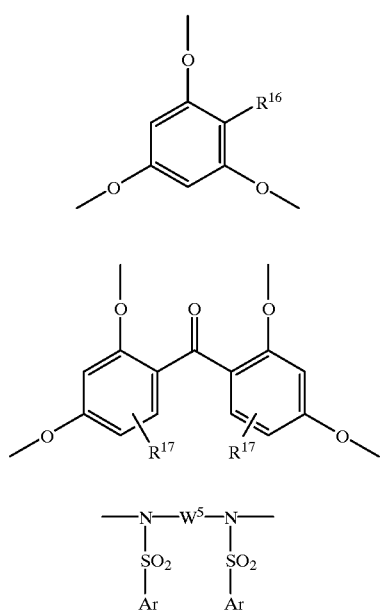

(X)

(XI)

In formula (II):

(II)

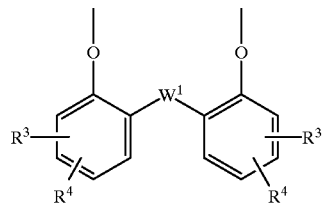

W¹ is an optional intervening group selected from the group consisting of imino group, oxygen atom, sulfur atom, an optionally substituted alkylene group, an optionally substituted arylene group, and carbonyl group, and W¹ may be absent. Preferably, W¹ is an optional intervening group selected from the group consisting of oxygen atom, sulfur atom, methylene group, and carbonyl group, and W¹ may be absent. More preferably, W¹ is an optionally present intervening group selected from the group consisting of sulfur atom, methylene group, and carbonyl group, and W¹ may be absent. Most preferably, W¹ is an optionally present intervening group which is methylene group or carbonyl group, and W¹ may be absent.

R³ and R⁴ may be either the same or different, and are selected from the group consisting of hydrogen atom, an alkyl group, an aryl group, an alkoxy group, a halogen atom, an acyl group, cyano group, and nitro group. Preferably, R³ and R⁴ are independently selected from hydrogen atom, an alkyl group, an aryl group, a halogen atom, and an acyl group. More preferably, R³ and R⁴ are respectively a hydrogen atom.

The most preferable examples of X represented by the formula (II) are those represented by the following formulae:

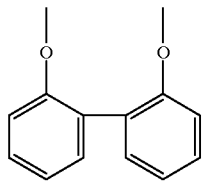

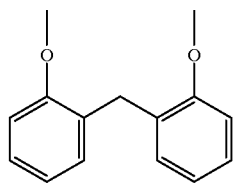

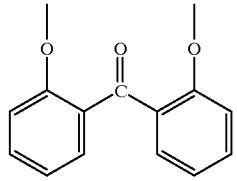

In formula (III):

(III)

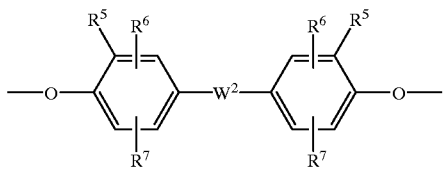

W² is an intervening group selected from imino group; oxygen atom; sulfur atom; sulfinyl group; sulfonyl group; optionally substituted methylene group; carbonyl group; a branched aliphatic group, a non-branched aliphatic group, an alicyclic group and an aromatic group, which may contain a hetero atom and whose hydrogen atom may be substituted with a hetero atom; and a combination thereof. Preferably, W² is an intervening group selected from sulfur atom; sulfinyl group; sulfonyl group; optionally substituted methylene group; carbonyl group; a branched aliphatic group, a non-branched aliphatic group, an alicyclic group and an aromatic group, which may contain a hetero atom and whose hydrogen atom may be substituted with a hetero atom; and a combination thereof. More preferably, W² is an intervening group selected from sulfur atom, sulfonyl group, methylene group, dimethylmethylene group, carbonyl group, 1,4-dioxobutylene group, 1,4-dioxohexylene group, and 1,10-diaza-4,7,13, 16-tetraoxacyclooctadecane having carbonyl group bonded to each of the nitrogen atoms at 1- and 10-positions. Most preferably, W² is an intervening group selected from sulfonyl group and 1,10-diaza-4,7,13, 16-tetraoxacyclooctadecane having a carbonyl group bonded to each of the nitrogen atoms at 1- and 10-positions.

R⁵ is selected from hydrogen atom, an alkyl group, an aryl group, an alkoxy group, a halogen atom, an acyl group, cyano group, and nitro group; and preferably, R⁵ is an alkyl group, an aryl group, an alkoxy group, a halogen atom, an acyl group, cyano group, and nitro group, and more preferably R⁵ is an alkyl group or an aryl group.

R⁶ and R⁷ may be either the same or different, and are respectively selected from the group consisting of hydrogen atom, an alkyl group, an aryl group, an alkoxy group, a halogen atom, an acyl group, cyano group, and nitro group. Preferably, $R^6$ and $R^7$ are independently selected from hydrogen atom, an alkyl group, an aryl group, an acyl group, and nitro group. More preferably, $R^5$ is methyl group, $R^6$ is hydrogen atom, and $R^7$ is methyl group or hydrogen atom.

The most preferable examples of X represented by the formula (III) are those represented by the following formulae:

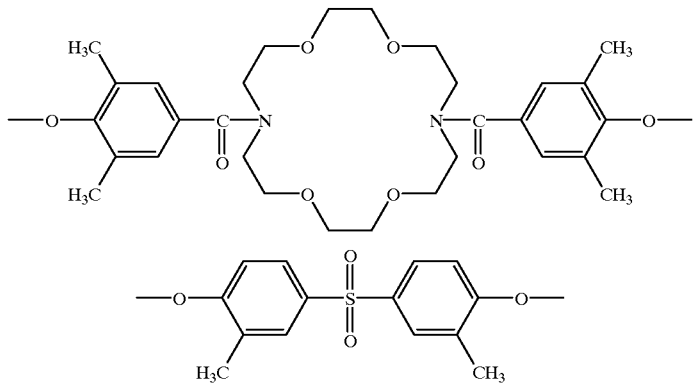

In formula (IV):

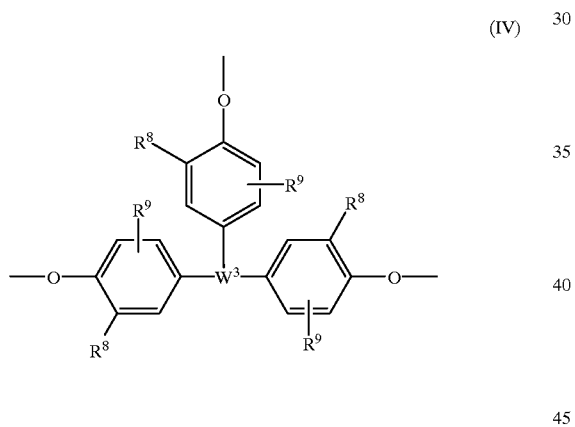

$W^3$ is an intervening group selected from methine group; nitrogen atom; a branched aliphatic group, a non-branched aliphatic group, an alicyclic group and an aromatic group, which may contain a hetero atom and whose hydrogen atom may be substituted with a hetero atom; and a combination thereof. Preferably, $W^3$ is an intervening group selected from methine group, a branched aliphatic group, a non-branched aliphatic group, an alicyclic group and an aromatic group which may contain a hetero atom and whose hydrogen atom may be substituted with a hetero atom, and a combination thereof. More preferably, $W^3$ is methine group.

$R^8$ and $R^9$ may be either the same or different, and are respectively selected from the group consisting of hydrogen atom, an alkyl group, an aryl group, an alkoxy group, a halogen atom, an acyl group, cyano group, and nitro group. Preferably, $R^8$ and $R^9$ are independently selected from the group consisting of hydrogen atom, an alkyl group, an aryl group, and an acyl group.

In formula (V):

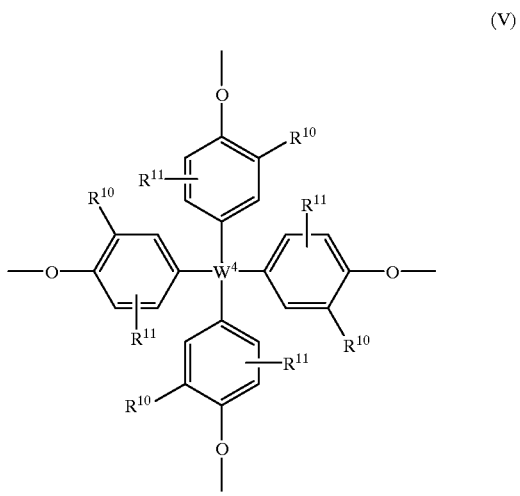

$W^4$ is an intervening group selected from carbon atom; a branched aliphatic group, a non-branched aliphatic group, an alicyclic group and an aromatic group, which may contain a hetero atom and whose hydrogen atom may be substituted with a hetero atom; and a combination thereof. Preferably, $W^4$ is an intervening group selected from a branched aliphatic group, a non-branched aliphatic group, an alicyclic group and an aromatic group which may contain a hetero atom and whose hydrogen atom may be substituted with a hetero atom; and a combination thereof.

$R^{10}$ and $R^{11}$ may be either the same or different, and are respectively selected from the group consisting of hydrogen atom, an alkyl group, an aryl group, an alkoxy group, a halogen atom, an acyl group, cyano group, and nitro group. Preferably, $R^{10}$ and $R^{11}$ are independently selected from the group consisting of hydrogen atom, an alkyl group, an aryl group, and an acyl group.

In formula (VI):

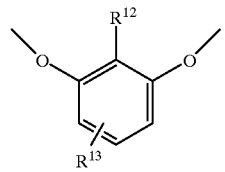

(VI)

$R^{12}$ is hydrogen atom, an alkyl group, an aryl group, an alkoxy group, a halogen atom, an acyl group, cyano group, and nitro group; and preferably, $R^{12}$ is an alkyl group or an aryl group. Most preferably, $R^{12}$ is methyl group.

$R^{13}$ is hydrogen atom, an alkyl group, an aryl group, an alkoxy group, a halogen atom, an acyl group, cyano group, or nitro group; and preferably, $R^{13}$ is hydrogen atom, an alkyl group, an aryl group, or an acyl group.

In formula (VII):

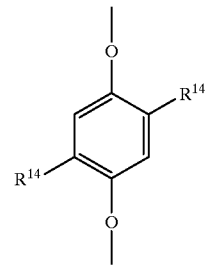

(VII)

$R^{14}$ is hydrogen atom, an alkyl group, an aryl group, an alkoxy group, a halogen atom, an acyl group, cyano group, or nitro group; and preferably, $R^{14}$ is an alkyl group, an aryl group, an alkoxy group, a halogen atom, an acyl group, cyano group, or nitro group; and more preferably, $R^{14}$ is an alkyl group or an aryl group.

In formula (VIII):

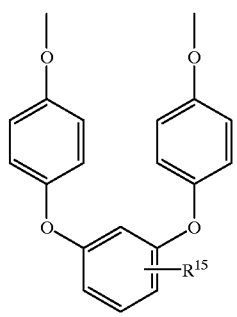

(VIII)

$R^{15}$ is hydrogen atom, an alkyl group, an aryl group, an alkoxy group, a halogen atom, an acyl group, cyano group, or nitro group; and preferably, $R^{15}$ is hydrogen atom, an alkyl group or an aryl group.

In formula (IX):

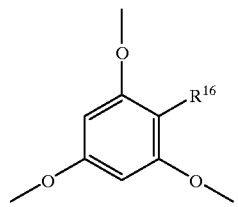

(IX)

$R^{16}$ is hydrogen atom, an alkyl group, an aryl group, an alkoxy group, a halogen atom, an acyl group, cyano group, or nitro group; and preferably, $R^{16}$ is an alkyl group, an aryl group, cyano group or an acyl group. More preferably, $R^{16}$ is an acyl group.

In formula (X):

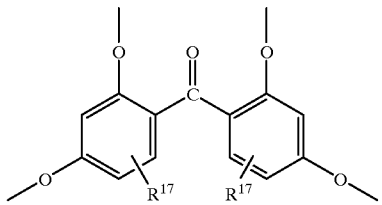

(X)

$R^{17}$ is hydrogen atom, an alkyl group, an aryl group, an alkoxy group, a halogen atom, an acyl group, cyano group, or nitro group; and preferably, $R^{17}$ is hydrogen atom, an alkyl group, an aryl group, or an acyl group.

In formula (XI):

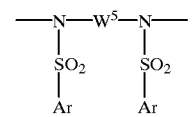

(XI)

$W^5$ is an intervening group selected from a branched aliphatic group, a non-branched aliphatic group, an alicyclic group and an aromatic group, which may contain a hetero atom and whose hydrogen atom may be substituted with a hetero atom; and a combination thereof; and preferably, $W^5$ is a branched aliphatic group, a non-branched aliphatic group, which may contain a hetero atom and whose hydrogen atom may be substituted with a hetero atom.

Ar is an aryl group, and preferably, Ar is p-tolyl group.

Exemplary alkyl groups for $R^3$ to $R^{17}$ include methyl group, ethyl group, propyl group, butyl group, and hexyl group.

Exemplary aryl groups for $R^3$ to $R^{17}$ include phenyl group and naphthyl group.

Exemplary alkoxy groups for $R^3$ to $R^{17}$ include methoxy group, ethoxy group, and phenoxy group.

Exemplary halogen atoms for $R^3$ to $R^{17}$ include fluorine atom, chlorine atom, and bromine atom.

Exemplary acyl groups for $R^3$ to $R^{17}$ include acetyl group, propionyl group, butyryl group and benzoyl group.

The acridinium compound of the present invention is characterized by its inclusion of 2 or more acridinium rings which function as luminescent groups; a binding group Z for the purpose of labeling that is bonded to the acridinium ring on the part of the nitrogen atom at 10-position in the acridinium ring; and a leaving group X free from binding group and having an aryloxy group or an arylsulfonamide group through which group X binds to carbonyl carbon bonded to the carbon atom at 9-position of the acridinium ring.

Preferably, Z is a hydrophilic group (and more preferably, Z is carboxyl group), and X is an aryloxy group which has a substituent selected from phenyl group, benzyl group, benzoyl group, or an alkyl group (e.g. methyl group) at its ortho position (2- and/or 6-position in the case of phenoxy group).

It is also preferable that Z is N-succinimidyl-oxycarbonyl group.

As a consequence of the above-described features, the acridinium compound of the present invention has the characteristic features as described above.

The acridinium compound of the present invention has at least 2 acridinium rings in one molecule, and since the acridinium ring is the luminescence group, the compound of the present invention exhibits high luminescence efficiency.

Furthermore, as demonstrated in Example 25, the acridinium compound of the present invention exhibits a luminescence higher than that of the compound, SAC-1 produced in Comparative Example 2 (the compound reported in Japanese Patent Application Laid-Open No. 6(1994)-158039) which also has 2 luminescence groups in one molecule. This fact indicates that the increase in the number of the luminescence group in one molecule is more efficiently reflected on the luminescence in the compound of the present invention.

In SAC-1 described in Japanese Patent Application Laid-Open No. 6(1994)-158039, 4-position of the phenoxy group is substituted with an electron donor group, and the luminescence efficiency is thereby reduced. This is a consequence of the presence on the phenoxy group of a functional group involved in the binding, which limits the freedom in the choice of the synthesis routes, and in turn the structure of the moiety. In contrast, n the acridinium ester compound of the present invention, a substituent can be readily introduced on the phenoxy group, and the luminescence intensity can be increased by introducing an effective substituent.

The acridinium compound of the present invention has a high stability. In Example 26, MDAC-1, which is the acridinium compound of the present invention, and SAC-1, which is the compound produced in Comparative Example 2, were compared for their stability. MDAC-1 exhibited a stability higher than that of SAC-1, and it is due to the absence of substituents on both 2- and 6-positions of the phenoxy group in the compounds of Japanese Patent Application Laid-Open No. 6(1994)-158039, leading to absence of the resistance to hydrolysis. This is also a consequence of the difficulty in synthesizing a compound having a substituent introduced on either 2- or 6-position in the compounds of Japanese Patent Application Laid-Open No. 6(1994)-158039.

The acridinium compound of the present invention also has a high labeling efficiency since the compound has 2 or more functional groups per one molecule that are involved in the binding with the compound to be labeled, namely, the functional groups (binding groups) for the labeling. It is believed that the acridinium compound of the present invention has a bonding efficiency with the compound to be labeled higher than that of the compounds of European Patent Application Laid-Open EP 609885A wherein only one functional group per one molecule is involved in the binding. Such higher labeling efficiency would enable reduction in the amount of the compound used for the labeling, and hence, reduction in the amount of the organic solvent added to the reaction solution for dissolution of the compound, and inactivation of the antibody or the like by the organic solvent is thereby prevented. In addition, reduction in the molar amount of the compound used during the labeling procedure would result in the reduced amount of the compound that are non-specifically adsorbed on the antibody or the like, and the influence of the non-specifically adsorbed compound that are undesirable for the assay may be decreased. The reduced molar amount of the compound used during the labeling procedure also results in the reduced amount of impurity after the labeling, and a convenient purification of the desired labeled antibody or the like is thereby enabled.

In the case of the acridinium compound of the present invention, the molar amount of the compound required for labeling is reduced. When the compound of the present invention and the compound of European Patent Application Laid-Open EP 609885A are respectively used for labeling an antibody so that the antibody is labeled with the same number of the acridinium residue, the molar amount of the compound required for the labeling in the case of the present compound would be ½, ⅓ . . . of that of the compounds of European Patent Application Laid-Open EP 609885A depending on the number of the acridinium residues present in one molecule. The reduced molar amount of the compound used during the labeling procedure would greatly reduce the inactivation of the antibody or the like by the organic solvent used for dissolution of the compound, as well as the undesirable influence of the non-specifically adsorbed compound. The purification procedure of the labeled antibody or the like would also be simplified as described in the foregoing.

The acridinium compound of the present invention retains its high luminescence efficiency even after undergoing the labeling procedure. In the case of the compounds of European Patent Application Laid-Open EP 609885A such as MAC-1, N—$CH_2$—COOH at 10-position of the acridinium ring is converted to N—$CH_2$—CONH— after the labeling of the antibody or the like with the compound. In contrast, in the case of the compound of the present invention, the 10-position of the acridinium ring which contains the substituent that became involved in the labeling is in the form of N—$CH_2$—CONH—, while the 10-position of the acridinium ring that was not involved in the labeling retains its N—$CH_2$—COOH form even after the labeling of the antibody or the like with the compound, and the conditions suitable for luminescence are thereby retained. In other words, when the acridinium ring of the same number is bonded to the antibody or the like, all of the 10-position of the acridinium rings would be in the state of N—$CH_2$—CONH— in the compounds of European Patent Application Laid-Open EP 609885A while the 10-positions of only ½, ⅓ . . . of the acridinium rings would be N—$CH_2$—CONH— and the 10-position of other acridinium rings would retain the N—$CH_2$—COOH form favorable for the luminescence in the compounds of the present invention.

In the labeling procedure using the acridinium compound of the present invention, increase in hydrophobicity of the antibody or the like is suppressed. When an antibody or the like is labeled with a compound of European Patent Application Laid-Open EP 609885A or Japanese Patent Application Laid-Open No. 6(1994)-158039, hydrophobicity of the antibody or the like is increased by the introduction of the acridinium ring into the antibody or the like. Such an increase in the hydrophobicity may induce decrease in the activity of the antibody as well as aggregation and precipitation of the antibody. In the case of the compound of the present invention, increase in the hydrophobicity is compensated by the introduction of the hydrophilic —COOH group when at least one —COOH group is introduced in the labeling procedure. In addition, —NH$_2$ and —SH groups in the antibody or the like are consumed in the labeling procedure, and since such groups are hydrophilic, the labeling procedure may be deemed as a procedure that decreases the hydrophilicity. When the acridinium residue of the same number is involved in the labeling, the number of the —NH2 and —SH groups consumed may be reduced in the case of the compound of the present invention to ½, ⅓ . . . of the case of the European Patent Application Laid-Open EP 609885A, and decrease in the number of hydrophilic groups may be suppressed.

The preferable acridinium compounds are MDAC-1 to MDAC 24 shown in FIGS. 4 to 10, and among such compounds, the compounds that can be most easily synthesized are MDAC-1, MDAC-2, MDAC-6, MDAC-8, and MDAC-16 in view of the availability of the starting materials and the simplicity of the synthesis procedure. These compounds are also provided with high chemiluminescence efficiency since they have 2 chemiluminescent acridinium residues of high luminescence activity per one molecule, and such high chemiluminescence efficiency is retained even after the labeling. These compounds are also convenient for use in the labeling of proteins, nucleic acids, and the like, and exhibit excellent stability upon use as a reagent. These compounds are, therefore, quite useful.

Next, typical processes for preparing the acridinium compounds of the present invention are described. The processes of the preparation, however, are not limited to any particular processes.

In the production of the acridinium compound of the formula (I), 1 mole of the compound having the moiety X is first reacted with 2 moles or excess of the compound having the group represented by formula (XII), and a compound having the group Z—A— such as Z—A—Y is then reacted with the nitrogen atom at 10-position of the acridine ring of the resulting compound to thereby produce the acridinium compound of the formula (I).

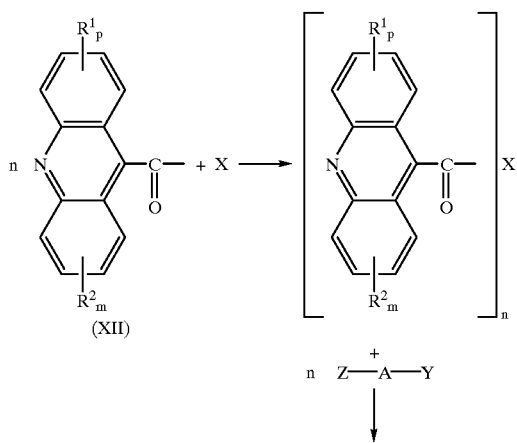

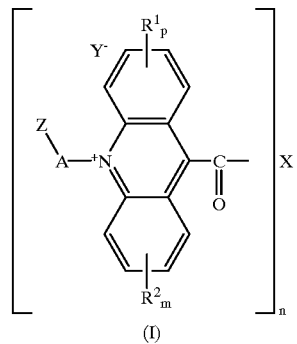

(I)

In this process, the leaving group X is bonded to the 2 or more acridine rings before the introduction of the functional group Z for the labeling, and therefore, the moiety of the leaving group X can be modified with any desired substituents, and a plurality of acridine rings can be bonded to one leaving group X, and in addition, the functional group for the labeling can be readily bonded to such acridine rings.

In a typical process for producing the acridinium ester compounds of the present invention having the leaving group X represented by formulae (II), (III), (IV), (V), (VI), (VII), (VIII), (IX) or (X), a compound (polyhydric arylalcohol) having 2 or more phenolic hydroxyl groups corresponding to the target acridinium ester compound and an acridinecarboxylic acid derivative are first reacted in the presence of a condensing agent to produce an aryl ester of the acridinecarboxylic acid. The nitrogen atom at 10-position of the acridine ring of the resulting aryl ester of the acridinecarboxylic acid is then alkylated with an alkylating agent to produce the acridinium ester compound.

More illustratively, a compound (polyhydric arylalcohol) having 2 or more phenolic hydroxyl groups and 9-chlorocarbonyl acridine are reacted in a solvent in the presence of a base to produce an aryl ester of an acridinecarboxylic acid. The bases which may be employed in this reaction include triethylamine and pyridine. An exemplary catalyst useful in this reaction is N,N-dimethylaminopyridine. Use of a small amount of N,N-dimethylaminopyridine will facilitate the reaction to be completed at room temperature in a short period. Exemplary solvents are chloroform, methylene chloride, ether and toluene, and the preferable solvent is methylene chloride.

Next, an alkylating agent having the functional group Z for the labeling protected with a protecting group is reacted with the aryl ester of acridinecarboxylic acid in the presence or absence of a solvent to produce an acridinium ester compound having a protected functional group for the labeling. Exemplary alkylating agents having the functional group Z for labeling protected with a protecting group include an alkyl halide substituted with a carboxylic acid protected with a substituted benzyl group or t-butyl group; and alkyl ester with the same protected carboxyl group of a superstrong acid such as trifluoromethanesulfonic acid, and preferably, the alkylating agent is alkyl ester with the same protected carboxyl group of trifluoromethanesulfonic acid. When the solvent is used in this reaction, the solvent used is typically methylene chloride, chloroform or 1,2-dichloroethane.

An acid catalyst is then reacted with the resulting acridinium ester compound having the protected functional group for the labeling in the presence or absence of a solvent to produce the acridinium ester compound of the present invention having the leaving group X represented by formulae (II), (III), (IV), (V), (VI), (VII), (VIII), (IX) or (X). When the solvent is used in this reaction, the solvent used is typically acetic acid, methylene chloride or phosphoric acid. Exemplary acid catalysts are hydrobromic acid and trifluoroacetic acid.

In a typical process for producing the acridinium acylsulfonamide compound of the present invention having the leaving group X represented by formulae (XI), a compound (polyamine compound) having 2 or more amino groups corresponding to the target acridinium acylsulfonamide compound and a sulfonic acid derivative are first reacted in the presence of a condensing agent to produce a compound (polysulfonic amide compound) having 2 or more sulfonamide groups. The compound (polysulfonic amide compound) having 2 or more sulfonamide groups is further reacted with an acridinecarboxylic acid derivative in the presence of a condensing agent to produce an acridinecarboxylic sulfonamide. The nitrogen atom at 10-position of the acridine ring of the resulting acridinecarboxylic sulfonamide is alkylated with an alkylating agent to produce the acridinium acylsulfonamide compound.

More illustratively, a compound (polyamine compound) having 2 or more amino groups and sulfonyl chloride are reacted in a solvent in the presence of a base to produce a compound (polysulfonic amide compound) having 2 or more sulfonamide groups. The bases which may be employed in this reaction include triethylamine and pyridine. Exemplary solvents are chloroform, methylene chloride, ether and toluene, and the preferable solvent is methylene chloride. The compound (polysulfonic amide compound) having 2 or more sulfonamide groups is then reacted with 9-chlorocarbonyl acridine in a solvent in the presence of a base to produce an acridinecarboxylic sulfonamide. The bases which may be employed in this reaction include triethylamine and pyridine. Use of a catalytic amount of N,N-dimethylaminopyridine is also useful in this reaction for accelerating the reaction. Exemplary solvents are chloroform, methylene chloride, ether and toluene, and the preferable solvent is methylene chloride.

Next, an alkylating agent having the functional group Z for the labeling protected with a protecting group is reacted with the acridinecarboxylic sulfonamide in the presence or absence of a solvent to produce an acridinium acylsulfonamide having a protected functional group for the labeling. Exemplary alkylating agents having the functional group Z for labeling protected with a protecting group include an alkyl halide substituted with a carboxylic acid protected with a substituted benzyl group or t-butyl group; and alkyl ester with the same protected carboxyl group of a superstrong acid such as trifluoromethanesulfonic acid, and preferably, the alkylating agent is alkyl ester with the same protected carboxyl group of trifluoromethanesulfonic acid. When the solvent is used in this reaction, the solvent used is typically methylene chloride, chloroform or 1,2-dichloroethane.

An acid catalyst is then reacted with the resulting acridinium acylsulfonamide compound having a protected functional group for the labeling in the presence or absence of a solvent to produce the acridinium acylsulfonamide compound of the present invention having the leaving group X represented by formulae (XI). When the solvent is used in this reaction, the solvent used is typically acetic acid, methylene chloride or phosphoric acid. Exemplary acid catalysts are hydrobromic acid and trifluoroacetic acid.

The conjugate of the present invention is a conjugate wherein the acridinium compound of the present invention has been covalently bonded to an antibody, an antigen, a hapten, a lectin, a sugar chain, a complex carbohydrate, a receptor, a ligand, an enzyme, a substrate, a polynucleotide (e.g. DNA or RNA), or the like through the functional group Z for the labeling of the acridinium compound of the present invention.

The conjugate of the present invention may be produced by binding the acridinium compound represented by the above-described formula (I) with the specific binding substance through conventional chemical reaction. For example, when the specific binding substance is a protein, and the binding site in the structure of the specific binding substance is amino group, exemplary preferable binding groups Z of the acridinium compound are $-SO_2Cl$, N-succinimidyl group, N-phthalimide group, $-COOH$, $-COCl$ and $-N=C=S$, and the binding of the binding group Z with the specific binding substance may be effected by a known method such as the one described in Eiji Ishikawa et al. ed., "Enzyme Immunoassay (3rd Edition) (in Japanese)", Igaku Shoin, 75–151 (1986). Exemplary such methods include those utilizing dehydration condensation reaction such as mixed acid anhydride method and active esterification method using N-hydtoxysuccinimide; and those utilizing addition reaction using thioisocyanate or azide.

For effecting an assay by using the compound of the present invention, the conjugate as described above is first prepared, and the assay is then effected by utilizing the specific binding reaction between the conjugate and the analyte in the sample. Exemplary assays that may be effected include an immunochemical assay wherein the analyte is an antigen, a hapten, or a specific antibody; a DNA probe assay wherein the target substance is a nucleic acid (polynucleotide); a receptor assay wherein a ligand is detected.

The compound and conjugate of the present invention are quite useful for such specific binding assay since they exhibit high luminescence efficiency and high stability.

Next, the present invention is described in detail by referring to Examples, which by no means limit the scope of the invention.

EXAMPLES

Example 1

(1) Synthesis of 2,2'-bis(acridine-9"-carbonyloxy)biphenyl

To 20 ml of thionyl chloride was suspended 0.84 g/3.74 mmol of acridine-9-carboxylic acid, and the suspension was refluxed under heat for 2 hours. Excessive thionyl chloride was distilled off the reaction mixture under reduced pressure to obtain 9-chlorocarbonyl acridine hydrochloride (1.0 g/96%). The resulting 9-chlorocarbonyl acridine hydrochloride and 0.3 g/1.61 mmol of 2,2'-biphenol were suspended in 50 ml of methylene chloride, and to this suspension were added 2 ml of triethylamine and a catalytic amount (44 mg/0.36 mmol) of dimethylaminopyridine in a stream of argon with stirring. The reaction mixture was stirred at room temperature for 2 hours, and then washed with 1N hydrochloric acid, distilled water, saturated aqueous solution of sodium hydrogencarbonate, and saturated aqueous solution of sodium chloride, in this order. The organic layer was dried with anhydrous sodium sulfate, and after removing the drying agent, the solvent was evaporated under reduced pressure. The residue was purified by silica gel column chromatography using hexane-methylene chloride for the eluting solution to obtain 0.85 g of the desired 2,2'-bis (acridine-9"-carbonyloxy)biphenyl. $^1$H-NMR (CDCl$_3$): δ7.34–7.75 (20H, m), 8.18 (4H, d, $J_H$=9 Hz).

(2) Synthesis of 2,2'-bis(10"-carboxymethylacridine-9"-carbonyloxy)biphenyl bistrifluoromethanesulfonate To 2 ml of methylene chloride was dissolved 100 mg/0.17 mmol of 2,2'-bis(acridine-9"-carbonyloxy)biphenyl produced in (1), and in a stream of argon, to this solution was added 500 mg/1.7 mmol of benzyloxycarbonylmethyl trifluoromethanesulfonate synthesized in accordance with Angew. Chem., 98, p264 (1986), and the mixture was stirred at room temperature for 4 days. Ether was added to the reaction mixture, and the resulting precipitate was separated by filtration and washed with ether. The resulting 2,2'-bis(10"-benzyloxycarbonylmethylacridine-9"-carbonyloxy) biphenyl bistrifluoromethanesulfonate was added to 5 ml of 30% hydrogen bromide/acetic acid solution, and the reaction mixture was stirred at 50° C. for 30 minutes. Ether was added to the reaction mixture, and the resulting precipitate was separated by filtration. The resulting precipitate was washed with ether, and purified with reverse phase HPLC (high performance liquid chromatography) to obtain 140 mg of the desired 2,2'-bis(10"-carboxymethylacridine-9"-carbonyloxy)biphenyl bistrifluoromethanesulfonate (hereinafter referred to as [MDAC-1]). MS: 714 ($M^+$).

Example 2

(1) Synthesis of 3,5-dimethyl-4-acetoxybenzoic acid

To 60 ml of benzene was suspended 10 g/60 mmol of 3,5-dimethyl-4-hydroxybenzoic acid, and 7.5 g/74 mmol of acetic anhydride and 150 μl of pyridine were added to the suspension. The reaction mixture was refluxed under heat for 12 hours, and allowed to stand at room temperature for 12 hours. The precipitated crystals were separated by filtration and washed with a small amount of benzene and air dried to obtain 7.1 g of the desired 3,5-dimethyl-4-acetoxybenzoic acid. $^1$H-NMR ($CDCl_3$): $\delta 2.22$ (6H, s), 2.37 (3H, s), 7.85 (2H, s), 11.53 (1H, s).

(2) Synthesis of 3,5-dimethyl-4-acetoxybenzoyl chloride

To 21 ml of thionyl chloride was suspended 9.3 g/45 mmol of 3,5-dimethyl-4-acetoxybenzoic acid, and the suspension was refluxed under heat for 90 minutes. After cooling to room temperature, excessive thionyl chloride was distilled off under reduced pressure to obtain 9.9 g of the desired 3,5-dimethyl-4-acetoxybenzoyl chloride.

(3) Synthesis of 1,10-bis(3',5'-dimethyl-4'-acetoxyphenylcarbonyl)-1,10-diaza-4,7,13,16-tetraoxacyclooctadecane To 50 ml of methylene chloride were dissolved 0.9 g/4 mmol of 3,5-dimethyl-4-acetoxybenzoyl chloride and 0.5 g/1.9 mmol of 1,10-diaza-4,7,13,16-tetraoxacyclooctadecane, and to this solution was added 2.2 ml of triethylamine and a catalytic amount (40 mg/0.3 mmol) of diethylaminopyridine in an ice bath. The reaction mixture was refluxed under heat for 4 hours, and allowed to cool to room temperature. The reaction solution was washed with 1N hydrochloric acid, distilled water, saturated aqueous solution of sodium hydrogencarbonate, and saturated aqueous solution of sodium chloride, in this order. The organic layer was dried with anhydrous sodium sulfate, and after removing the drying agent, the solvent was evaporated under reduced pressure. The residue was purified by silica gel column chromatography using methylene chloride-methanol for the eluting solution to obtain 1.1 g of the desired 1,10-bis(3',5'-dimethyl-4'-acetoxyphenylcarbonyl)-1,10-diaza-4,7,13,16-tetraoxacyclooctadecane. MS: 642 ($M^+$), 451, 191. $^1$H-NMR ($CDCl_3$): $\delta 2.15$ (6H, s), 2.34 (12H, s), 3.6 (16H, br), 3.8 (8H, br), 7.05 (4H, s).

(4) Synthesis of 1,10-bis(3',5'-dimethyl-4'-hydroxyphenylcarbonyl)-1,10-diaza-4,7,13,16-tetraoxacyclooctadecane To 40 ml of mixed solvent of anhydrous methanolmethylene chloride was dissolved 0.5 g/0.8 mmol of 1,10-bis(3',5'-dimethyl-4'-acetoxyphenylcarbonyl)-1,10-diaza-4,7,13,16-tetraoxacyclooctadecane, and the solution was cooled to 0° C. To this solution was added 2.6 ml of freshly prepared 1M methanol solution of sodium methoxide, and the mixture was stirred at 0° C. for 2 hours. After adding Amberlite 15 until the reaction solution became neutral, the resin was separated by filtration and the filtrate was concentrated under reduced pressure to obtain 0.4 g of 1,10-bis(3',5'-dimethyl-4'-hydroxyphenylcarbonyl)-1,10-diaza-4,7,13,16-tetraoxacyclooctadecane. $^1$H-NMR ($CDCl_3$): $\delta 2.15$ (12H, s), 3.6 (16H, br), 3.8 (8H, br), 5.89 (2H, s), 6.90 (4H, s).

(5) Synthesis of 1,10-bis[3',5'-dimethyl-4'-(acridine-9"-carbonyloxy)phenylcarbonyl]-1,10-diaza-4,7,13,16-tetraoxacyclooctadecane 0.49 g of the desired 1,10-bis[3',5'-dimethyl-4'-(acridine-9"-carbonyloxy)phenylcarbonyl]-1,10-diaza-4,7,13,16-tetraoxacyclooctadecane was obtained from 350 mg/1.26 mmol of 9-chlorocarbonyl acridine hydrochloride and 350 mg/0.63 mmol of 1,10-bis(3',5'-dimethyl-4'-hydroxyphenylcarbonyl)-1,10-diaza-4,7,13,16-tetraoxacyclooctadecane by repeating the procedure of Example 1(1). MS: 968 ($M^+$), $^1$H-NMR ($CDCl_3$): $\delta 2.44$ (12H, s), 3.7 (16H, br), 3.8 (8H, br), 7.26 (4H, s), 7.7–8.4 (16H, m).

(6) Synthesis of 1,10-bis[3',5'-dimethyl-4'-(10"-carboxymethylacridinium-9"-carbonyloxy)phenylcarbonyl]-1,10-diaza-4,7,13,16-tetraoxacyclooctadecane bistrifluoromethanesulfonate Using 0.16 g/0.16 mmol of 1,10-bis[3',5'-dimethyl-4'-(acridine-9"-carbonyloxy)phenylcarbonyl]-1,10-diaza-4,7,13,16-tetraoxacyclooctadecane for the starting material, 86.4 mg of the desired 1,10-bis[3',5'-dimethyl-4'-(10"-carboxymethylacridinium-9"-carbonyloxy)phenylcarbonyl]-1,10-diaza-4,7,13,16-tetraoxacyclooctadecane bistrifluoromethanesulfonate (hereinafter referred to as [MDAC-2]) was obtained by repeating the procedure of Example 1(2). MS: 1086 ($M^+$).

Example 3

(1) Synthesis of bis[3,5-dimethyl-4-(acridine-9'-carbonyloxy)phenyl]sulfone 0.57 g of the desired bis[3,5-dimethyl-4-(acridine-9'-carbonyloxy)phenyl]sulfone was obtained from 500 mg/1.8 mmol of 9-chlorocarbonyl acridine hydrochloride and 280 mg/0.9 mmol of bis(3,5-dimethyl-4-hydroxyphenyl)sulfone by repeating the procedure of Example 1(1). $^1$H-NMR ($CDCl_3$): $\delta 2.53$ (12H, s), 7.66–7.72 (4H, m), 7.84–7.88 (8H, m), 8.33–8.41 (8H, m).

(2) Synthesis of bis[3,5-dimethyl-4-(10'-carboxymethylacridinium-9'-carbonyloxy)phenyl]sulfone bistrifluoromethanesulfonate 0.10 g/0.14 mmol of bis[3,5-dimethyl-4-(acridine-9'-carbonyloxy)phenyl]sulfone was used for the starting material, and 85.5 mg of the desired bis[3,5-dimethyl-4-(10'-carboxymethylacridinium-9'-carbonyloxy)phenyl]sulfone bistrifluoromethanesulfonate (hereinafter referred to as [MDAC-3]) was obtained by repeating the procedure of Example 1(2). MS: 834 ($M^+$).

Example 4

(1) Synthesis of 2,2-bis[3'-methyl-4'-(acridine-9"-carbonyloxy)phenyl]propane 0.54 g of the desired 2,2-bis[3'-methyl-4'-(acridine-9"-carbonyloxy)phenyl]propane was obtained from 500 mg/1.8 mmol of 9-chlorocarbonyl acridine hydrochloride and 230 mg/0.9 mmol of 2,2-bis(3'-methyl-4'-hydroxyphenyl) propane by repeating the procedure of Example 1(1). $^1$H-NMR ($CDCl_3$): $\delta 1.78$ (6H, s), 2.39 (6H, s), 7.29–8.31 (22H, m).

(2) Synthesis of 2,2-bis[3'-methyl-4'-(10"-carboxymethyl-acridinium-9"-carbonyloxy)phenyl]propane bistrifluoromethanesulfonate 0.10 g/0.15 mmol of 2,2-bis[3'-methyl-4'-(acridine-9"-carbonyloxy)phenyl]propane was used for the starting material, and 129 mg of the desired 2,2-bis[3'-methyl-4'-(10"-carboxymethylacridinium-9"-carbonyloxy)phenyls propane bistrifluoromethanesulfonate (hereinafter referred to as [MDAC-4]) was obtained by repeating the procedure of Example 1(2). MS: 784 (M$^+$).

Example 5

(1) Synthesis of bis[3-methyl-4-(acridine-9'-carbonyloxy)phenyl]sulfide 0.53 g of the desired bis[3-methyl-4-(acridine-9'-carbonyloxy)phenyl]sulfide was obtained from 500 mg/1.8 mmol of 9-chlorocarbonyl acridine hydrochloride and 220 mg/0.9 mmol of bis(3-methyl-4-hydroxyphenyl)sulfide by repeating the procedure of Example 1(1). $^1$H-NMR (CDCl$_3$): δ2.39 (6H, s), 7.44–8.30 (22H, m).

(2) Synthesis of bis[3-methyl-4-(10'-carboxymethylacridinium-9'-carbonyloxy)phenyl]sulfide bistrifluoromethanesulfonate 0.10 g/0.15 mmol of bis[3-methyl-4-(acridine-9'-carbonyloxy)phenyl]sulfide was used for the starting material, and 134 mg of the desired bis[3-methyl-4-(10'-carboxymethylacridinium-9'-carbonyloxy)phenyl]sulfide bistrifluoromethanesulfonate (hereinafter referred to as [MDAC-5]) was obtained by repeating the procedure of Example 1(2). MS: 774 (M$^+$).

Example 6

(1) Synthesis of 2,2'-bis(acridine-9"-carbonyloxy)benzophenone 0.52 g of the desired 2,2'-bis(acridine-9"-carbonyloxy)benzophenone was obtained from 500 mg/1.8 mmol of 9-chlorocarbonyl acridine hydrochloride and 190 mg/0.9 mmol of 2,2'-dihydroxybenzophenone by repeating the procedure of Example 1(1). $^1$H-NMR (CDCl$_3$): δ7.49–7.94 (16H, m), 8.21–8.28 (8H, m).

(2) Synthesis of 2,2'-bis(10"-carboxymethylacridinium-9"-carbonyloxy)benzophenone bistrifluoromethanesulfonate 0.10 g/0.16 mmol of 2,2'-bis(acridine-9"-carbonyloxy)benzophenone was used for the starting material, and 160 mg of the desired 2,2'-bis(10"-carboxymethylacridinium-9"-carbonyloxy)benzophenone bistrifluoromethanesulfonate (hereinafter referred to as [MDAC-6]) was obtained by repeating the procedure of Example 1(2). MS: 742 (M$^+$).

Example 7

(1) Synthesis of 4,4'-dihydroxy-3,3',5,5'-tetramethylbenzophenone

To 20 ml methanol was dissolved 500 mg/2.0 mmol of bis(4-hydroxy-3,5-dimethylphenyl)methane, and 886 mg/4.0 mmol of dicyanodichloroquinone was added to the solution at once in a stream of argon. After stirring at room temperature for 1 hour, the solvent was distilled off under reduced pressure. The residue was dissolved in ethyl acetate, and the insoluble matter was separated by filtration and re-concentrated. The resulting crude product was purified by silica gel column chromatography using methylene chloride for the eluting solution to obtain 230 mg of the desired 4,4'-dihydroxy-3,3',5,5'-tetramethylbenzophenone. MS: 270 (M$^+$), $^1$H-NMR (CDCl$_3$/DMSO-d$^6$): δ2.29 (12H, s), 7.41 (4H, s), 7.96 (2H, s).

(2) Synthesis of 4,4'-bis(acridine-9"-carbonyloxy)-3,3',5,5'-tetramethylbenzophenone 0.28 g of the desired 4,4'-bis(acridine-9"-carbonyloxy)-3,3',5,5'-tetramethylbenzophenone was obtained from 300 mg/1.1 mmol of 9-chlorocarbonyl acridine hydrochloride and 120 mg/0.45 mmol of 4,4'-dihydroxy-3,3',5,5'-tetramethylbenzophenone by repeating the procedure of Example 1(1). $^1$H-NMR (CDCl$_3$): δ2.55 (12H, s), 7.69–7.73 (8H, m), 7.86–7.92 (4H, m), 8.40 (4H, d, J$_H$=9 Hz), 8.47 (4H, d, JH$_H$=9 Hz).

(3) Synthesis of 4,4'-bis(10"-carboxymethylacridinium-9"-carbonyloxy)-3,3',5,5'-tetramethylbenzophenone bistrifluoromethanesulfonate 0.10 g/0.08 mmol of 4,4'-bis(acridine-9"-carbonyloxy)-3,3',5,5'-tetramethylbenzophenone was used for the starting material, and 147 mg of the desired 4,4'-bis(10"-carboxymethylacridinium-9"-carbonyloxy)-3,3',5,5'-tetramethylbenzophenone bistrifluoromethanesulfonate (hereinafter referred to as [MDAC-7]) was obtained by repeating the procedure of Example 1(2). MS: 798 (M$^+$).

Example 8

(1) Synthesis of bis[2'-(acridine-9-carbonyloxy)phenyl]methane 0.50 g of the desired bis[2-(acridine-9'-carbonyloxy)phenyl]methane was obtained from 500 mg/1.8 mmol of 9-chlorocarbonyl acridine hydrochloride and 180 mg/0.9 mmol of bis(2-hydroxyphenyl)methane by repeating the procedure of Example 1(1). $^1$H-NMR (CDCl$_3$): δ4.14 (2H, s), 7.23–7.55 (12H, mn), 7.69–7.75 (4H, m), 7.87 (4H, d, J$_H$=9 Hz), 8.20 (4H, d, J$_H$=9 Hz).

(2) Synthesis of bis[2-(10'-carboxymethylacridinium-9'-carbonyloxy) phenyl]methane bistrifluoromethanesulfonate 0.10 g/0.16 mmol of bis[2-(acridine-9'-carbonyloxy)phenyl]methane was used for the starting material, and 147 mg of the desired bis2-(10'-carboxymethylacridinium-9-carbonyloxy) phenyl]methane bistrifluoromethanesulfonate (hereinafter referred to as [MDAC-8]) was obtained by repeating the procedure of Example 1(2). MS: 728 (M$^+$).

Example 9

(1) Synthesis of 2,6-bis(acridine-9'-carbonyloxy)toluene 0.50 g of the desired 2,6-bis(acridine-9'-carbonyloxy)toluene was obtained from 500 mg/1.8 mmol of chlorocarbonyl acridine hydrochloride and 112 mg/0.9 mmol of 2,6-dihydroxytoluene by repeating the procedure of Example 1(1). $^1$H-NMR (DMSO-d$^6$): δ2.37 (3H, s), 7.84–8.05 (12H, m), 8.32–8.39 (7H, m).

(2) Synthesis of 2,6-bis(10'-carboxymethylacridinium-9'-carbonyloxy)toluene bistrifluoromethanesulfonate 0.10 g/0.19 mmol of 2,6-bis(acridine-9'-carbonyloxy)toluene was used for the starting material, and 133 mg of the desired 2,6-bis(10'-carboxymethylacridinium-9'-carbonyloxy)toluene bistrifluoromethanesulfonate (hereinafter referred to as [MDAC-9]) was obtained by repeating the procedure of Example 1(2). MS: 652 (M$^+$).

Example 10

(1) Synthesis of 2,2'-bis(2",7"-dimethoxyacridine-9"-carbonyloxy)biphenyl

To methylene chloride was suspended 0.15 g/0.44 mmol of 9-chlorocarbonyl-2,7-dimethoxyacridine hydrochloride synthesized in accordance with Anal. Chem. Acta., 205, p267 (1988) and 39 mg/0.21 mmol of 2,2'-biphenol, and to this suspension were added 0.3 ml of triethylamine and a catalytic amount of (10 mg/0.08 mmol) of 4-dimethylaminopyridine in a stream of argon with stirring. The reaction mixture was stirred at room temperature for 2 hours, and washed with 1N hydrochloric acid, distilled water, saturated aqueous solution of sodium hydrogencarbonate, and saturated aqueous solution of sodium chloride, in this order. The organic layer was dried with anhydrous sodium sulfate, and after removing the drying agent, the solvent was evaporated under reduced pressure. The residue was purified by silica gel column chromatography using methylene chloride for the eluting solution to obtain 105 mg of the desired 2,'-bis(2',7"-dimethoxyacridine-9"-carbonyloxy)biphenyl. $^1$H-NMR (CDCl$_3$): δ3.67 (12H, s), 7.04 (4H, d, J$_H$=3 Hz)s, 7.22–7.63 (10H, m), 7.99–8.07 (6H, m).

(2) Synthesis of 2,2'-bis(2",7"-dimethoxy-10"-carboxymethylacridine-9"-carbonyloxy)biphenyl bistrifluoromethanesulfonate To methylene chloride was dissolved 50 mg/0.07 mmol of 2,2-bis(2",7"-dimethoxyacridine-9"-carbonyloxy)biphenyl produced in (1), and to this solution was added 210 mg/0.7 mmol of benzyloxycarbonylmethyl trifluoromethanesulfonate in a stream of argon, and the mixture was stirred at room temperature for 7 days. Ether was added to the reaction mixture, and the resulting precipitate was separated by filtration and was hed with ether. The resulting 2,2'-bis(2",7"-dimethoxy-10"-benzyloxycarbonylmethylacridine-9"-carbonyloxy)biphenyl bistrifluoromethanesulfonate was added to 2 ml of 30% hydrogen bromide/acetic acid solution, and the reaction mixture was stirred at 50° C. for 30 minutes. Ether was added to the reaction mixture, and the resulting precipitate was separated by filtration. The precipitate was washed with ether, and purified with reverse phase HPLC to obtain 70 mg of the desired 2,2'-bis( 2",7"-dimethoxy-10"-carboxymethylacridine-9"-carbonyloxy) biphenyl bistrifluoromethanesulfonate (hereinafter referred to as [MDAC-10]). MS: 834 (M$^+$).

Example 11

(1) Synthesis of tris[4-(acridine-9'-carbonyloxy)phenyl]methane

To methylene chloride were suspended 500 mg/1.8 mmol of 9-chlorocarbonyl acridine hydrochloride synthesized in accordance with Example 1(1) and 175 mg/0.6 mmol of tris(4-hydroxyphenyl)methane, and 1 ml of triethylamine and a catalytic amount of (27 mg/0.22 mmol) of 4-dimethylaminopyridine were added to the suspension in argon atmosphere. The reaction mixture was stirred at room temperature for 24 hours, and the precipitated crystals were separated by filtration. The crystals were washed with a small amount of methylene chloride and air dried to obtain 0.34 g of the desired tris[4-(acridine-9'-carbonyloxy)phenyl] methane. MS: 907 (M$^+$).

(2) Synthesis of tris[4-(10'-carboxymethylacridinium-9'-carbonyloxy)phenyl]methane tristrifluoromethanesulfonate 0.05 g/0.06 mmol of tris[4-(acridine-9'-carbonyloxy)-phenyl]methane was used for the starting material, and 74 mg of the desired tris[4-(10'-carboxymethylacridinium-9'-carboxy)phenyl]methane tristrifluoromethanesulfonate (hereinafter referred to as [MDAC-11]) was obtained by repeating the procedure of Example 1(2). MS: 1084 (M$^+$).

Example 12

(1) Synthesis of benzyl ester of 5-hydroxypentanoic acid

To 100 ml of 1N aqueous sodium hydroxide solution was added 10 g/0.1 mol of δ-valerolactone, and the mixture was stirred at 65° C. for 12 hours. The reaction mixture was allowed to cool to room temperature, and the water was distilled off under reduced pressure. The resulting white crystals were dried at 60° C. under reduced pressure for 24 hours to completely remove the water. 13.8 g of sodium salt of 5-hydroxypentanoic acid was obtained. The sodium salt of 5-hydroxypentanoic acid was suspended in 75 ml of acetone, and to this suspension were added 33.7 g/0.2 mol of benzyl bromide and 1.6 g/4.9 mmol of tetra-N-butylammonium bromide, and the mixture was stirred at 45° C. for 24 hours. After distilling off the solvent, 500 ml of ethyl acetate was added, and the solution was washed with 1M aqueous solution of sodium hydrogensulfate and saturated aqueous solution of sodium hydrogencarbonate, in this order. The organic layer was dried with anhydrous sodium sulfate, and after removing the drying agent, the solvent was evaporated under reduced pressure. The residue was purified by silica gel column chromatography using methylene chloride for the eluting solution to obtain 6.3 g of the desired benzyl ester of 5-hydroxypentanoic acid.

(2) Synthesis of 4-benzyloxycarbonylbutyl trifluoromethanesulfonate 20 ml solution of 0.98 ml of anyhydrous pyridine in methylene chloride was cooled to −22° C. in argon atmosphere, and 3.4 g/12.1 mmol of trifluoromethanesulfonic acid was slowly added to this solution with stirring. Five minutes after the addition, 10 ml solution of 2.4 g/11.5 mmol of the benzyl ester of 5-hydroxypentanoic acid in methylene chloride was added to the solution at once. After the addition, the solution was stirred at −22° C. for 15 minutes, and then, at room temperature for 60 minutes. Insoluble matters were separated by filtration and the solvent was distilled off under reduced pressure. The residue was purified by silica gel column chromatography using hexanemethylene chloride for the eluting solution to obtain 0.7 g of the desired 4-benzyloxycarbonylbutyl trifluoromethanesulfonate.

(3) Synthesis of 2,2'-bis(10"-carboxybutylacridinium-9"-carbonyloxy)biphenyl bistrifluoromethanesulfonate To 5 ml of methylene chloride was dissolved 100 mg/0.17 mmol of 2,2'-bis(acridine-9"-carbonyloxy)biphenyl produced in Example 1(1), and to this solution was added 650 mg/1.9 mmol of benzyloxycarbonylbutyl trifluoromethanesulfonate in a stream of argon, and the mixture was stirred at room temperature for 10 days. Ether was added to the reaction mixture, and the resulting precipitate was separated by filtration and washed with ether. The resulting 2,2'-bis(10"-benzyloxycarbonylbutylacridinium-9"-carbonyloxy) biphenyl bistrifluoromethanesulfonate was added to 5 ml of 30% hydrogen bromide/acetic acid solution, and the reaction mixture was stirred at 50° C. f or 30 minutes. Ether was added to the reaction mixture, and the resulting precipitate was separated by filtration. The thus separated precipitate was washed with ether, and purified with reverse phase HPLC to obtain 140 mg of the desired 2,2 '-bis(10"-carboxybutylacridinium-9"-carbonyloxy)biphenyl bistrifluoromethanesulfonate (hereinafter referred to as [MDAC-12]). MS: 798 (M$^+$).

Example 13

(1) Synthesis of 1,10-diaza-1,10-bis(4'-methylphenylsulfonyl)decane

To 15 ml of methylene chloride was dissolved 2.6 g/13.9 5mol of p-toluenesulfonyl chloride, and the solution was cooled to 0° C., and 1.9 ml of triethylamine and 20 mg/0.16 mmol of 4-dimethylaminopyridine were slowly added to the solution. Solution of 1.0 g/6.9 mmol of 1,8-diaminooctane in methylene chloride was added to the solution and allowed to react at room temperature for 18 hours. The solvent was distilled off the reaction solution under reduced pressure, and the residue was triturated with ether. The ether layer was removed by decanting and the residue was dissolved in methylene chloride, and the solution was washed with distilled water, and the organic layer was dried with anhydrous sodium sulfate. After removing the drying agent, the solvent was distilled off under reduced pressure. The residue was triturated again with ether, and the precipitated crystals were separated by filtration to obtain 2.2 g of the desired 1,10-diaza-1,10-bis(4'-methylphenylsulfonyl)decane. $^1$H-NMR (CDCl$_3$): δ1.17 (8H, br), 1.42 (4H, mr), 2.42 (6H,), 2.89 (4H, dd, $J_H$=6 Hz, 7 Hz), 4.66 (2H, t, $J_H$=6 Hz), 7.73 (4H, d, $J_H$=2 Hz), 7. 76 (4H, d, $J_H$=2 Hz).

(2) Synthesis of 1,10-diaza-1,10-bis(acridine-9'-carbonyl)-1,10-bis(4"-methylphenylsulfonyl)decane 0.42 g of the desired 1,10-diaza-1,10-bis(acridine-9'-carbonyl)-1,10-bis(4"-methylphenylsulfonyl)decane was obtained from 680 mg/2.4 mmol of 9-chlorocarbonyl acridine hydrochloride and 0.55 g/1.2 mmol of 1,10-diaza-1,10-bis(4'-methylphenylsulfonyl)decane by repeating the procedure of Example 1(1). $^1$H-NNR (CDCl$_3$): δ1.17 (8H, br), 1.42 (4H, br), 2.42 (6H, s), 2.90 (4H, m), 7.27–8.25 (24H, m).

(3) Synthesis of 1,10-diaza-1,10-bis(10'-carboxymethylacridinium-9'-carbonyl)-1,10-bis(4"-methylphenylsulfonate)decane bistrifluoromethanesulfonate 0.10 g/0.12 mmol of 1,10-diaza-1,10-bis(acridine-9'-carbonyl)-1,10-bis(4"-methylphenylsulfonyl)decane was used for the starting material, and 61 mg of the desired 1,10-diaza-1,10-bis(10'-carboxymethylacridinium-9'-carbonyl)1,10-bis(4"-methylphenylsulfonate)decane bistrifluoromethanesulfonate (hereinafter referred to as [MDAC-13]) was obtained by repeating the procedure of Example 1(2). MS: 980 (M$^+$).

Example 14

(1) Synthesis of 1,10-diaza-4,7-dioxa-1,10-bis(4'-methylphenylsulfonyl)decane 1.6 g of the desired 1,10-diaza-4,7-dioxa-1,10-bis(4'-methylphenylsulfonyl)decane was obtained from 1.3 g/6.8 mmol of p-toluenesulfonyl chloride and 0.5 g/3.4 mmol of 1,10-diaza-4,7-dioxa-decane by repeating the procedure of Example 13(1). $^1$H-NMR (CDCl$_3$): δ2.42 (6H, s), 3.12 (4H, m), 3.53 (8H, t, $J_H$=5 Hz), 5.48 (2H, t, $J_H$=5 Hz), 7.74 (4H, d, $J_H$=2 Hz), 7.76 (4H, d, $J_H$=2 Hz).

(2) Synthesis of 1,10-diaza-4,7-dioxa-1,10-bis(acridine-9'-carbonyl)-1,10-bis(4"-methylphenylsulfonyl)decane 0.94 g of the desired 1,10-diaza-4,7-dioxa-1,10-bis(acridine-9'-carbonyl)-1,10-bis(4"-methylphenylsulfonyl) decane was obtained from 1.5 g/5.4 mmol of 9-chlorocarbonyl acridine hydrochloride and 1.0 g/2.2 mmol of 1,10-diaza-4,7-dioxa-1,10-bis(4'-methylphenylsulfonate) decane by repeating the procedure of Example 1(1). MS: 866 (M$^+$).

(3) Synthesis of 1,10-diaza-4,7-dioxa-1,10-bis(10'-carboxymethylacridinium-9'-carbonyl)-1,10-bis(4"-methylphenylsulfonyl)decane bistrifluoromethanesulfonate 0.10 g/0.12 mmol of 1,10-diaza-4,7-dioxa-1,10-bis (acridine-9'-carbonyl)-1,10-bis(4"-methylphenylsulfonyl) decane was used for the starting material, and 22 mg of the desired 1,10-diaza-4,7-dioxa-1,10-bis(10'-carboxymethylacridinium-9'-carbonyl)-1,10-bis(4"-methylphenylsulfonate)decane bistrifluoromethanesulfonate (hereinafter referred to as [MDAC-14]) was obtained by repeating the procedure of Example 1(2). MS: 984 (M$^+$).

Example 15

(1) Synthesis of bis[3-methyl-4-(4'-nitrobenzoyloxy)phenyl] sulfide

To 50 ml of anhydrous pyridine was suspended 11.3 g/45.9 mmol of bis[3-methyl-4-hydroxyphenyl]sulfide, and 17.0 g/91.6 mmol of p-nitrobenzoylchloride was slowly added to the suspension. After completing the addition, the mixture was refluxed under heat for one hour, and allowed to stand at room temperature overnight for precipitation of the crystals. The crystals were placed in 400 ml of iced water, separated by filtration, washed with 5% aqueous solution of sodium hydrogencarbonate, 0.5N hydrochloric acid and water, in this order, and air dried. The crystals were recrystalized in toluene to obtain 23.3 g of the desired bis[3-methyl-4-(4'-nitrobenzoyloxy)phenyl]sulfide.

(2) Synthesis of bis[3-methyl-4-(4'-nitrobenzoyloxy)phenyl] sulfoxide

To dry chloroform was suspended 5.44 g/10 mmol of bis[3-methyl-4-(4'-nitrobenzoyloxy)phenyl]sulfide, and the suspension was cooled to 0° C. in ice-methanol bath. After adding 1.73 g/10 mmol of m-chloroperbenzoic acid, the mixture was stirred at room temperature for 2 days. The reaction mixture was washed twice with 5% aqueous solution of sodium hydrogencarbonate and once with saturated aqueous solution of sodium chloride, and dried with anhydrous sodium sulfate, and then, the solvent was distilled off under reduced pressure. The residue was purified by silica gel column chromatography using hexane-methylene chloride for the eluting solution to obtain 2.77 g of the desired bis[3-methyl-4-(4'-nitrobenzoyloxy)phenyl]sulfoxide.

(3) Synthesis of bis[3-methyl-4-hydroxyphenyl]sulfoxide

To ethanol was suspended 1 g/1.8 mmol of bis[3-methyl-4-(4'-nitrobenzoyloxy)phenyl]sulfoxide, and 350 mg/5.4 mmol of potassium hydroxide was added to the suspension and the suspension was stirred at 50° C. for 1 hour. The solvent in the reaction mixture was reduced to about ⅓ by distillation and 1N hydrochloric acid was added to precipitate the crystals. The crystals were separated by filtration, washed thoroughly with water, and air dried. The crystals were purified by silica gel column chromatography using hexane-methylene chloride for the eluting solution to obtain 0.37 g of the desired bis[3-methyl-4-hydroxyphenyl] sulfoxide.

(4) Synthesis of bis[3-methyl-4-(acridine-9'-carbonyloxy)-phenyl]sulfoxide 0.43 g of the desired bis[3-methyl-4-(acridine-9'-carbonyloxy)phenyl]sulfoxide was obtained from 500 mg/1.8 mmol of 9-chlorocarbonyl acridine hydrochloride synthesized in accordance with Example 1(1) and 200 mg/0.8 mmol of bis[3-methyl-4-hydroxyphenyl]sulfoxide.

(5) Synthesis of bis[3-methyl-4-(10'-carboxymethylacridinium-9'-carbonyloxy)phenyl]sulfoxide bistrifluoromethanesulfonate 0.03 g/0.05 mmol of bis[3-methyl-4-(acridine-9'-carbonyloxy)phenyl]sulfoxide was used for the starting material, and 20 mg of the desired bis[3-methyl-4-(10'-carboxymethylacridinium-9'-carbonyloxy)phenyl]sulfoxide bistrifluoromethanesulfonate (hereinafter referred to as [MDAC-15]) was obtained by repeating the procedure of Example 1(2). MS: 790 (M$^+$).

Example 16

(1) Synthesis of bis[3-methyl-4-(4'-nitrobenzoyloxy)-phenyl]sulfone

To dry chloroform was suspended 5.44 g/10 mmol of bis[3-methyl-4-(4'-nitrobenzoyloxy)phenyl]fulfide synthesized example 15 (1), and the suspension was cooled to 0° C. in ice-methanol bath. After adding 4.31 g/25 mmol of m-chloroperbenzoic acid, the mixture was brought back to room temperature and stirred for 4 days. The reaction mixture was washed twice with 5% aqueous solution of sodium hydrogencarbonate and once with saturated aqueous solution of sodium chloride, and dried with anhydrous sodium sulfate, and then, the solvent was distilled off under reduced pressure. Upon recrystalization of the residue from chloroform-toluene, there was obtained 4.85 g of the desired bis[3-methyl-4-(4'-nitrobenzoyloxy)phenyl]sulfone. $^1$H-NMR (DMSO-d$^6$): δ 2.30 (6H, s), 7.58 (2H, m), 7.95 (2H, m), 8.05 (2H, m), 8.41 (8H, m).

(2) Synthesis of bis[3-methyl-4-hydroxyphenyl]sulfone

To ethanol was suspended 3.76 g/6.5 mmol of bis[3-methyl-4-(4'-nitrobenzoyloxy)phenyl]sulfone, and 1.28 g/19.6 mmol of potassium hydroxide was added to the suspension and the suspension was stirred at room temperature for 1 hour. The solvent in the reaction mixture was reduced to about ⅓ under reduced pressure and 1N hydrochloric acid was added to precipitate the crystals. The crystals were separated by filtration, washed thoroughly with water, and air dried. the crystals were purified by silica gel column chromatography using hexane-methylene chloride for the eluting solution to obtain 1.29 g of the desired bis[3-methyl-4-hydroxyphenyl]sulfone.

(3) Synthesis of bis[3-methyl-4-(acridine-9'-carbonyloxy)-phenyl]sulfone 0.50 g of the desired bis[3-methyl-4-(acridine-9'-carbonyloxy)phenyl]sulfone was obtained from 500 mg/1.8 mmol of 9-chlorocarbonyl acridine hydrochloride synthesized in accordance with Example 1(1) and 210 mg/0.8 mmol of bis[3-methyl-4-hydroxyphenyl]sulfone.

(4) Synthesis of bis[3-methyl-4-(10'-carboxymethyl-acridinium-9'-carbonyloxy)phenyl]sulfone bistrifluoromethanesulfonate 0.03 g/0.04 mmol of bis[3-methyl-4-(acridine-9'-carbonyloxy)phenyl]sulfone was used for the starting material, and 27 mg of the desired bis[3-methyl-4-(10'-carboxymethylacridinium-9'-carbonyloxy)phenyl]sulfone bistrifluoromethanesulfonate (hereinafter referred to as [MDAC-16]) was obtained by repeating the procedure of Example 1(2). MS: 806 (M$^+$)

Example 17

(1) Synthesis of 1,3-bis[4'-(acridine-9"-carbonyloxy)-phenoxy]benzene 0.22 g of the desired 1,3-bis[4'-(acridine-9"-carbonyloxy)phenoxy]benzene was obtained from 500 mg/1.8 mmol of 9-chlorocarbonyl acridine hydrochloride synthesized in accordance with Example 1(1) and 250 mg/0.9 mmol of 1,3-bis(4'-hydroxyphenoxy)benzene.

(2) Synthesis of 1,3-bis[4'-(10"-carboxymethylacridinium-9"-carbonyloxy)phenoxy]benzene bistrifluoromethanesulfonate 0.05 g/0.08 mmol of 1,3-bis[4'-(acridine-9"-carbonyloxy)phenoxy]benzene was used for the starting material, and 17 mg of the desired 1,3-bis[4'-(10"-carboxymethylacridinium-9"-carbonyloxy)phenoxy]benzene bistrifluoromethanesulfonate (hereinafter referred to as [MDAC-17]) was obtained by repeating the procedure of Example 1(2). MS: 822 (M$^+$)

Example 18

(1) Synthesis of 2,4,6-tris(acridine-9'-carbonyloxy)-propiophenone 0.06 g of the desired 2,4,6-tris(acridine-9'-carbonyloxy)propiophenone was obtained from 500 mg/1.8 mmol of 9-chlorocarbonyl acridine hydrochloride synthesized in accordance with Example 1(1) and 100 mg/0.6 mmol of 2,4,6-trishydroxypropiophenone.

(2) Synthesis of 2,4,6-tris(10'-carboxymethylacridinium-9'-carbonyloxy)propiophenone bistrifluoromethanesulfonate 0.04 g/0.05 mmol of 2,4,6-tris(acridine-9'-carbonyloxy)propiophenone was used for the starting material, and 7 mg of the desired 2,4,6-tris(10'-carboxymethylacridinium-9'-carbonyloxy)propiophenone bistrifluoromethanesulfonate (hereinafter referred to as [MDAC-18]) was obtained by repeating the procedure of Example 1(2). MS: 974 (M$^+$).

Example 19

(1) Synthesis of bis[2-(acridine-9'-carbonyloxy)-5-chlorophenyl]methane 0.46 g of the desired bis[2-(acridine-9'-carbonyloxy)-5-chlorophenyl]methane was obtained from 600 mg/2.2 mmol of 9-chlorocarbonyl acridine hydrochloride synthesized in accordance with Example 1(1) and 240 mg/0.9 mmol of bis[2-hydroxy-5'-chlorophenyl]methane. $^1$H-NMR (CDCl$_3$): δ 3.99 (2H, s), 7.18 (2H, m), 7.40 (8H, m), 7.72 (4H, m), 7.82 (4H, m), 8.20 (4H, m).

(2) Synthesis of bis[2-(10'-carboxymethylacridinium-9'-carbonyloxy)-5-chlorophenyl]methane bistrifluoromethanesulfonate 0.1 g/0.15 mmol of bis[2-(acridine-9'-carbonyloxy)-5-chlorophenyl]methane was used for the starting material, and 116 mg of the desired bis[2-(10'-carboxymethyl-acridinium-9'-carbonyloxy)-5-chlorophenyl]methane bistrifluoromethanesulfonate (hereinafter referred to as [MDAC-19]) was obtained by repeating the procedure of Example 1(2). MS: 796, 798, 800 (M$^+$)

Example 20

(1) Synthesis of 3,3',5,5'-tetrachloro-2,2'-bis[acridine-9"-carbonyloxy]diphenylsulfide 0.25 g of the desired 3,3',5,5'-tetrachloro-2,2'-bis[acridine-9"-carbonyloxy]diphenylsulfide was obtained from 600 mg/2.2 mmol of 9-chlorocarbonyl acridine hydrochloride synthesized in accordance with Example 1(1) and 320 mg/0.9 mmol of 3,3',5,5'-tetrachloro- 2,2'-dihydroxydiphenylsulfide. $^1$H-NMR (CDCl$_3$): δ 7.32 (2H, m), 7.49 (6H, m), 7.76 (4H, m), 8.26 (4H, m), 8.46 (4H, m).

(2) Synthesis of 3,3',5,5'-tetrachloro-2,2'-bis[10"-carboxymethylacridinium-9"-carbonyloxy]diphenylsulfide bistrifluoromethanesulfonate 0.1 g/0.13 mmol of 3,3',5,5'-tetrachloro-2,2'-bis[acridine-9"-carbonyloxy]diphenylsulfide was used for the starting material, and 80 mg of the desired 3,3',5,5'-tetrachloro-2,2'-bis[10"-carboxymethylacridinium-9"-carbonyloxy]diphenylsulfide bistrifluoromethanesulfonate (hereinafter referred to as [MDAC-20]) was obtained by repeating the procedure of Example 1(2). MS: 882, 884, 886, 888 (M$^+$).

Example 21

(1) Synthesis of 2,5-diphenyl-1,4-dihydroxybenzene

To dry THF was dissolved 0.5 g/1.9 mmol of 2,5-diphenylbenzoquinone in argon atmosphere, and 85 mg/2.24 mmol of lithium aluminum hydride was added to the solution. After stirring at room temperature for 30 minutes, the reaction solution was added to ice containing 1N hydrochloric acid, and the mixture was allowed to stand for 30 minutes. The aqueous layer was extracted with ethyl acetate once, and the extract was dried with anhydrous sodium sulfate. The solvent was distilled off under reduced pressure, and the residue was purified by silica, gel column chromatography using hexane-methylene chloride for the eluting solution to obtain 0.28 g of the desired 2,5-diphenyl-1,4-dihydroxybenzene. $^1$H-NNR (CDCl$_3$+DMSO-d$^6$): δ 4.52 (2H, br), 6.91 (2H, s), 7.33 (6H, m), 7.61 (4H, m).

(2) Synthesis of 1,4-bis(acridine-9'-carbonyloxy)-2,5-diphenylbenzene

To 50 ml of methylene chloride were suspended 560 mg/2.0 mmol of 9-chlorocarbonyl acridine hydrochloride synthesized in accordance with Example 1(1) and 220 mg/0.8 mmol of 2,5-diphenyl-1,4-dihydroxybenzene, and to the solution were added 1 ml of triethylamine and a catalytic amount (25 mg/0.20 mmol) of dimethylaminopyridine in a stream of argon with stirring. The reaction mixture was stirred overnight at room temperature, and the precipitated crystals were separated by filtration. The crystals were washed several times with methylene chloride, and air dried to obtain 0.49 g of 1,4-bis(acridine-9'-carbonyloxy)-2,5-diphenylbenzene.

(3) Synthesis of 1,4-bis(10'-carboxymethylacridinium-9'-carbonyloxy)-2,5-diphenylbenzene bistrifluoromethane-sulfonate 0.1 g/0.15 mmol of 1,4-bis(acridine-9'-carbonyloxy)-2,5-diphenylbenzene was used for the starting material, and 120 mg of the desired 1,4-bis(10'-carboxymethylacridinium-9'-carbonyloxy)-2,5-diphenylbenzene bistrifluoromethane-sulfonate (hereinafter referred to as [MDAC-21]) was obtained by repeating the procedure of Example 1(2). MS: 790 (M$^+$).

Example 22
(1) Synthesis of 2,2',4,4'-tetrakis[]acridine-9"-carbonyloxy]benzophenone 0.37 g of the desired 2,2',4,4'-tetrakis[acridine-9"-carbonyloxy]benzophenone was obtained from 500 mg/1.8 mmol of 9-chlorocarbonyl acridine hydrochloride synthesized in accordance with Example 1(1) and 98 mg/0.4 mmol of 2,2',4,4'-tetrahydroxybenzophenone.

(2) Synthesis of 2,2',4,4'-tetrakis[10"-carboxymethyl-acridinium-9"-carbonyloxy]benzophenone tetrakistrifluoro-methanesulfonate 0.02 g/0.02 mmol of 2,2',4,4'-tetrakis[acridine-9"-carbonyloxy]benzophenone was used for the starting material, and 6 mg of the desired 2,2',4,4'-tetrakis[10"-carboxymethylacridinium-9"-carbonyloxy]benzophenone tetrakistrifluoromethanesulfonate (hereinafter referred to as [MDAC-22]) was obtained by repeating the procedure of Example 1(2). MS: 1302 (M$^+$).

Example 23
(1) Synthesis of 1,6-bis(3',5'-dimethyl-4'-hydroxyphenyl)-hexane-1,6-dione To 300 ml of methylene chloride was dissolved 10 g/82 mmol of 2,6-dimethylphenol, and the solution was cooled to 0° C. in sodium chloride-ice bath. After adding 49 g/368 mmol of anhydrous aluminum chloride, methylene chloride solution of 7.3 g/40 mmol of adipic dichloride was added dropwise to the mixture with thorough stirring while maintaining the temperature to not more than 5° C. The reaction mixture was added to 50 ml of ice containing conc. hydrochloric acid to decompose excessive anhydrous aluminum chloride, and the mixture was extracted twice with methylene chloride. The organic layer was washed with saturated sodium chloride solution, and dried with anhydrous sodium sulfate, and the solvent was distilled off under reduced pressure. The residue was recrystalized from toluene to obtain 2.5 g of 1,6-bis(3',5'-dimethyl-4'-hydroxyphenyl)hexane-1,6-dione. MS: 354 (M$^+$).

(2) Synthesis of 1,6-bis[3',5'-dimethyl-4'-(acridine-9'-carbonyloxy)phenyl]hexane-1,6-dione 0.17 g of the desired 1,6-bis[3',5'-dimethyl-4'-(acridine-9'-carbonyloxy)phenyl]hexane-1,6-dione was obtained from 171 mg/0.6 mmol of 9-chlorocarbonyl acridine hydrochloride synthesized in accordance with Example 1(1) and 100 mg/0.28 mmol of 1,6-bis(3',5'-dimethyl-4'-hydroxyphenyl)hexane-1,6-dione. MS: 764 (M$^+$).

(3) Synthesis of 1,6-bis[3',5'-dimethyl-4'-(10"-carboxy-methylacridinium-9"-carbonyloxy)phenyl]hexane-1,6-dione bistrifluoromethanesulfonate 0.5 g/0.065 mmol of 1,6-bis[3',5'-dimethyl-4'-(acridine-9"-carbonyloxy)phenyl]hexane-1,6-dione was used for the starting material, and 27 mg of the desired 1,6-bis[3',5'-dimethyl-4'-(10'-carboxymethylacridinium-9"-carbonyloxy)phenyl]hexane-1,6-dione bistrifluoromethane-sulfonate (hereinafter referred to as [MDAC-23]) was obtained by repeating the procedure of Example 1(2). MS: 882 (M$^+$).

Example 24
(1) Synthesis of 1,4-bis(3',5'-dimethyl-4'-hydroxyphenyl)-butane-1,4-dione To 300 ml of methylene chloride was dissolved 10 g/82 mmol of 2,6-dimethylphenol and 6.2 g/40 mmol of succinic dichloride, and the solution was cooled to 0° C. in sodium chloride-ice bath. 49 g/368 mmol of anhydrous aluminum chloride was added dropwise to the mixture with thorough stirring while maintaining the temperature to not more than 5° C. After completing the addition, the mixture was stirred at 5° C. for one hour, and at room temperature for 15 hours. The reaction mixture was then added to 50 ml of ice containing conc. hydrochloric acid to decompose excessive anhydrous aluminum chloride, and the mixture was extracted twice with methylene chloride. The organic layer was washed with saturated sodium chloride solution, and dried with anhydrous sodium sulfate, and the solvent was distilled off under reduced pressure. The residue was recrystalized from toluene to obtain 2.0 g of 1,4-bis(3',5'-dimethyl-4'-hydroxyphenyl)butane-1,4-dione. MS: 326 (M$^+$).

(2) Synthesis of 1,4-bis[3',5'-dimethyl-4'-(acridine-9"-carbonyloxy)phenyl]butane-1,4-dione 0.40 g of the desired 1,4-bis[3',5'-dimethyl-4'-(acridine-9"-carbonyloxy)phenyl]butane-1,4-dione was obtained from 500 mg/1.8 mmol of 9-chlorocarbonyl acridine hydrochloride synthesized in accordance with Example 1(1) and 280 mg/0.86 mmol of 1,4-bis(3',5'-dimethyl-4'-hydroxyphenyl)butane-1,4-dione. MS: 736 (M$^+$).

(3) Synthesis of 1,4-bis[3',5'-dimethyl-4'-(10"-carboxy-methylacridinium-9"-carbonyloxy)phenyl]butane-1,4-dione bistrifluoromethanesulfonate 0.5 g/0.054 mmol of 1,4-bis[3',5'-dimethyl-4'-(acridine-9"-carbonyloxy)phenyl]butane-1,4-dione was used for the starting material, and 27 mg of the desired 1,4-bis[3',5'-dimethyl-4'-(10"-carboxymethylacridinium-9"-carbonyloxy)phenyl]butane-1,4-dione bistrifluoro-methanesulfonate (hereinafter referred to as [MDAC-24]) was obtained by repeating the procedure of Example 1(2). MS: 854 (M$^+$).

Comparative Example 1
(1) Synthesis of 2'-methylphenyl acridine-9-carboxylate 0.33 g of the desired 2'-methylphenyl acridine-9-carboxylate was obtained from 500 mg/1.8 mmol of 9-chlorocarbonyl acridine hydrochloride and 200 mg/1.9 mmol of orthocresol in accordance with Example 1(1). MS: 313 (M$^+$), $^1$H-NMR(CDCl3): δ 2.37 (3H, s), 7.3–8.3 (12H, m).

(2) Synthesis of 2'-methylphenyl 10-carboxymethyl-acridinium-9-carboxylate trifluoromethanesulfonate 0.14 g/0.45 mmol of 2'-methylphenyl acridine-9-carboxylate was used for the starting material, and 202 mg of the desired 2'-methylphenyl acridinium-9-carboxylate trifluoromethanesulfonate (hereinafter referred to as [MAC-1]) was obtained by repeating the procedure of Example 1(2). MS: 372 (M$^+$).

Comparative Example 2
(1) Synthesis of 4,4-bis(4'-hydroxyphenyl)pentanoic acid (4"-maleimide)anilide To 2.6 ml of N,N-dimethylformamide was dissolved 0.49 g/1.71 mmol of 4,4-bis(4'-hydroxyphenyl)pentanoic acid and 0.35 g/1.86 mmol of N-(4-aminophenyl)maleimide, and 0.34 g/1.65 mmol of dicyclohexylcarbodiimide (DCC) was added to the solution in an ice bath. The mixture was stirred for one hour in an ice bath, and 5 hours at room temperature. The solvent was distilled off the reaction mixture using a vacuum pump, and the residue was purified by silica gel column chromatography using methylene chloride-methanol for the eluting solution to obtain 0.52 g of the desired 4,4-bis(4'-hydroxyphenyl)pentanoic acid (4"-maleimide)anilide, MS: 456 (M$^+$).

(2) Synthesis of 4,4-bis{4'-(acridine-9"-phenyl-carboxylate)}pentanoic acid (4'"-maleimide)anilide 700 mg of the desired 4,4-bis{4'-(acridine-9"-phenyl-carboxylate)}pentanoic acid (4'"-maleimide)anilide was obtained from 500 mg/1.8 mmol of 9-chlorocarbonyl acridine hydrochloride and 410 mg/0.9 mmol of 4,4-bis(4'-hydroxyphenyl)pentanoic acid (4"-maleimide)anilide in accordance with Example 1(1). MS: 866 ($M^+$).

(3) Synthesis of 4,4-bis{4'-(10"-methylacridiniumfluorosulfonate-9"-phenylcarboxylate)}pentanoic acid (4'"-maleimide)anilide 100 g/0.12 mmol of 4,4-bis{4'-(acridine-9"-phenylcarboxylate)}pentanoic acid (4'"-maleimide)anilide obtained in (2) was dissolved in 2 ml of anhydrous chloroform, and 140 mg/1.2 mmol of methyl ester of fluorosulfonic acid was added to the solution in a stream of argon, and the mixture was stirred at room temperature for one day. Ether was added to the reaction mixture, and the resulting precipitate was separated by filtration and washed to obtain the desired 4,4-bis{4'-(10"-methyl-acridiniumfluorosulfonate-9"-phenylcarboxylate)}pentanoic acid (4'"-maleimide)anilide (hereinafter referred to as [SAC-1]) was obtained. MS: 896 ($M^+$).

Example 25

The acridinium compounds MDAC-1 to MDAC 24, MAC-1 and SAC-1 produced in the above described Examples 1 to 24 and Comparative Examples 1 and 2 were respectively dissolved in DMF to prepare $\times 10^{-3}$M solutions. Each of the thus prepared solution was diluted with PBS (phosphate-buffered saline, pH 6.4) to $1\times 10^{-9}$M. To 10 µl of each diluted solution was added 300 µl of 0.5% hydrogen peroxide/0.1N nitric acid solution, and then, 300 µl of 0.125% cetyltrimethylammonium chloride/0.25N sodium hydroxide, and the chemiluminescence was measured for 2 seconds with a chemiluminescence measuring apparatus, AutoLumat LB953 (Berthold, FRG). The thus measured luminescence of the compounds is shown in Table 1 in terms of the luminescence per 1 mole compound (counts/mole).

TABLE 1

| Compound | Luminescence (counts/mole) | Compound | Luminescence (counts/mole) |
| --- | --- | --- | --- |
| MDAC-1 | $5.8 \times 10^{20}$ | MDAC-14 | $1.2 \times 10^{20}$ |
| MDAC-2 | $3.3 \times 10^{20}$ | MDAC-15 | $1.6 \times 10^{20}$ |
| MDAC-3 | $1.6 \times 10^{20}$ | MDAC-16 | $4.0 \times 10^{20}$ |
| MDAC-4 | $1.9 \times 10^{20}$ | MDAC-17 | $2.9 \times 10^{20}$ |
| MDAC-5 | $1.5 \times 10^{20}$ | MDAC-18 | $1.3 \times 10^{20}$ |
| MDAC-6 | $3.8 \times 10^{20}$ | MDAC-19 | $1.0 \times 10^{20}$ |
| MDAC-7 | $1.7 \times 10^{20}$ | MDAC-20 | $1.0 \times 10^{20}$ |
| MDAC-8 | $4.2 \times 10^{20}$ | MDAC-21 | $1.0 \times 10^{20}$ |
| MDAC-9 | $2.4 \times 10^{20}$ | MDAC-22 | $1.5 \times 10^{20}$ |
| MDAC-10 | $3.3 \times 10^{20}$ | MDAC-23 | $2.5 \times 10^{20}$ |
| MDAC-11 | $1.2 \times 10^{20}$ | MDAC-24 | $2.4 \times 10^{20}$ |
| MDAC-12 | $3.0 \times 10^{20}$ | MAC-L | $0.6 \times 10^{20}$ |
| MDAC-13 | $1.1 \times 10^{20}$ | SAC-1 | $0.8 \times 10^{20}$ |

Example 26

MDAC-1 produced in Example 1 and SAC-1 produced in Comparative Example 2 were respectively dissolved in DMF to prepare $1\times 10^{-3}$M solutions. The solution was diluted with 5 mM PB (phosphate buffer, pH 8.0) to prepare $1\times 10^{-7}$M solution. The solution was stored at 45° C. for one week in the dark. Each of the thus stored solution was diluted to $1\times 10^{-9}$M with 5 mM PB, pH 8.0, and measured for chemiluminescence in accordance with Example 25. Residual luminescence activity (%) after a predetermined period of storage was calculated for use as an index of stability, by the following equation (a):

Residual luminescence activity (%) =

$$\frac{\text{(Luminescence after storage)}}{\text{(Luminescence immediately after preparation)}} \times 100$$

Figure 3:
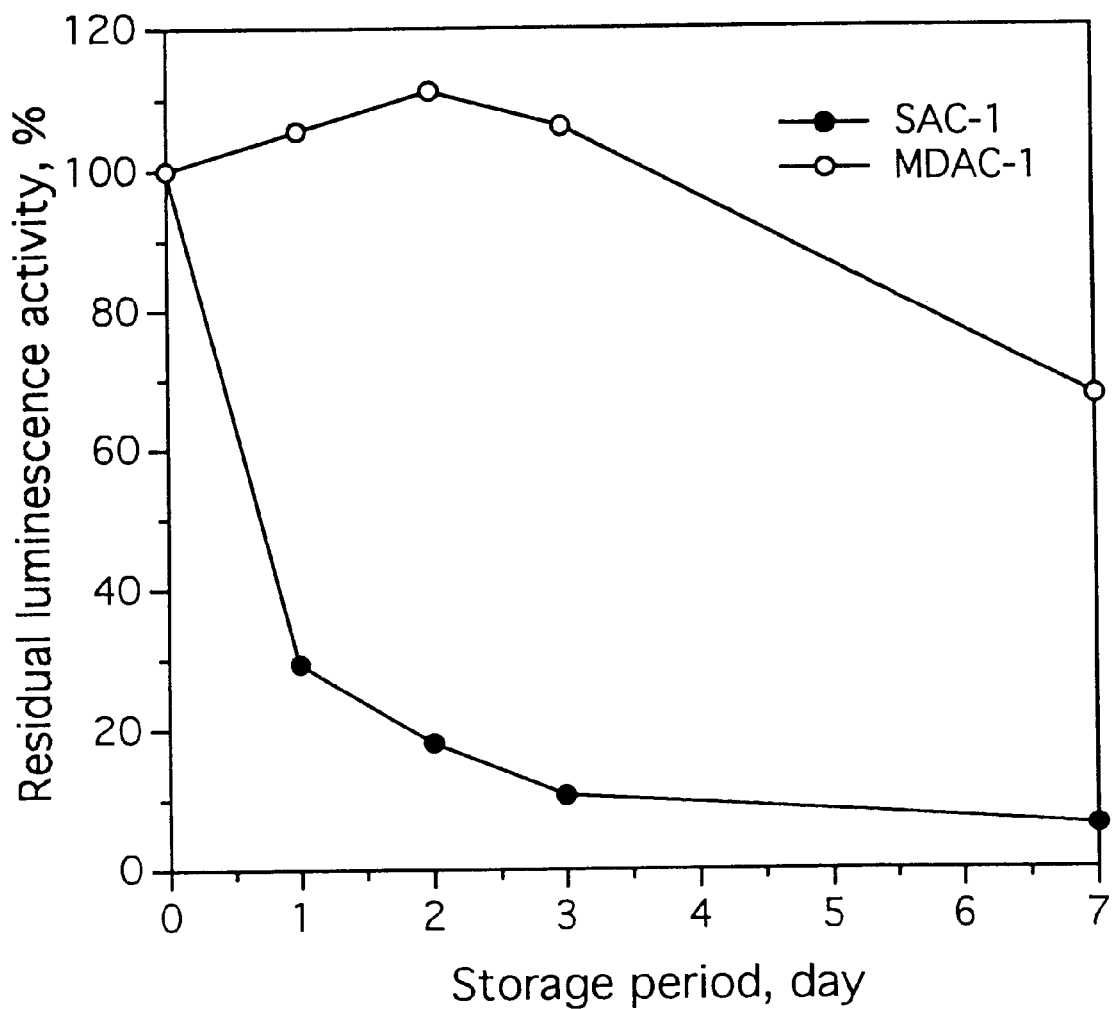
FIG. 3 is a graph showing stability of the acridinium compound.
Figure 4:
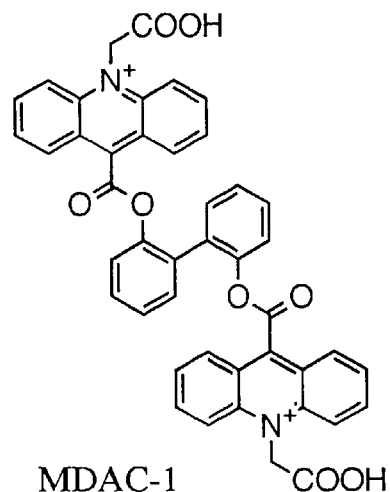
FIG. 4 shows chemical formulae of the acridinium compounds of the present invention synthesized in Examples 1 to 4.
Figure 4:
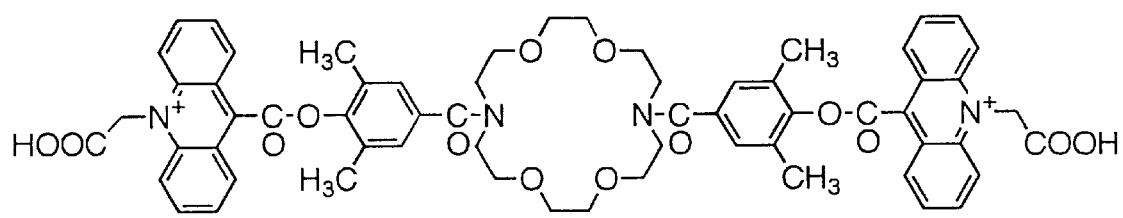
Figure 4:
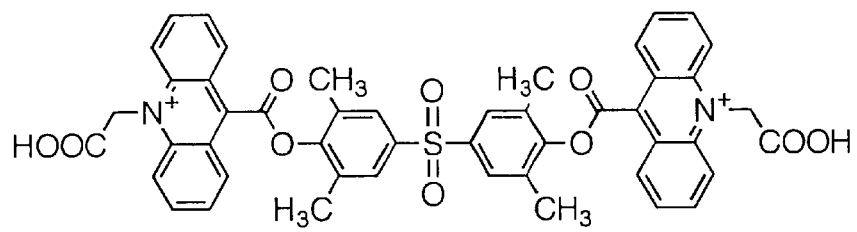
Figure 4:
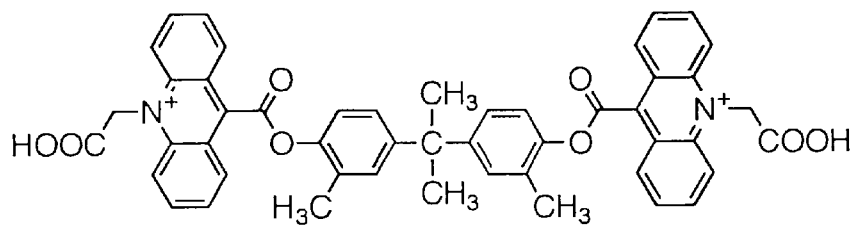
Figure 5:
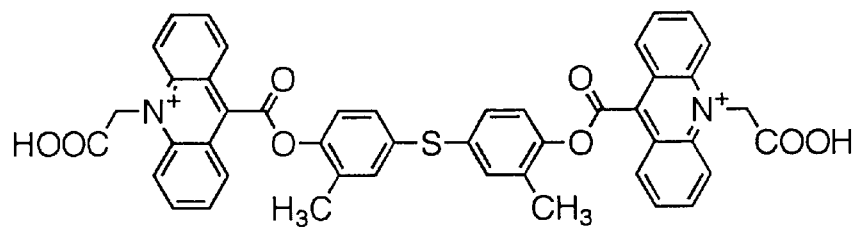
FIG. 5 shows chemical formulae of the acridinium compounds of the present invention synthesized in Examples 5 to 8.
Figure 5:
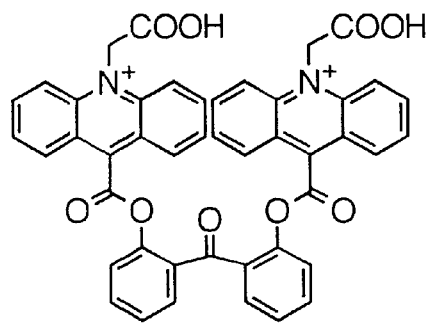
Figure 5:
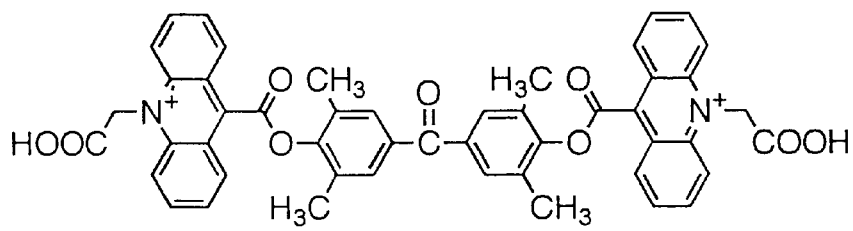
Figure 5:
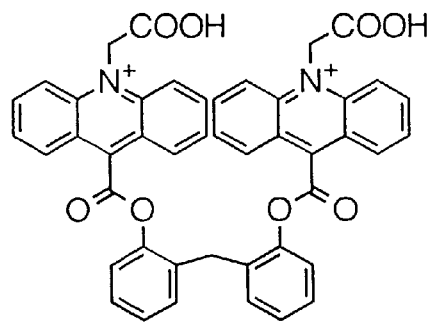
Figure 6:
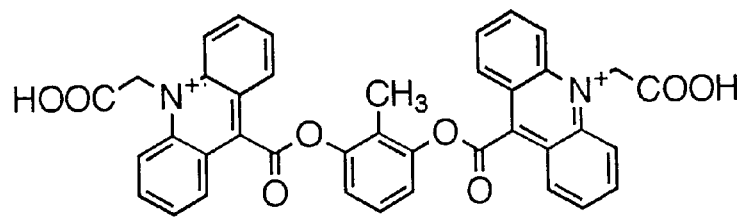
FIG. 6 shows chemical formulae of the acridinium compounds of the present invention synthesized in Examples 9 to 11.
Figure 6:
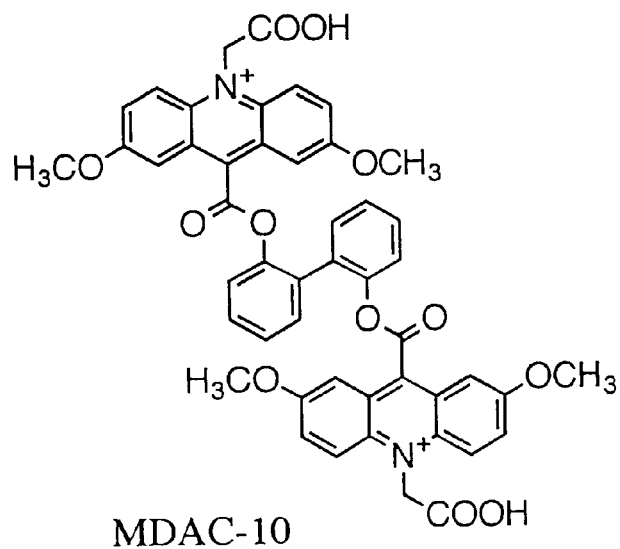
Figure 6:
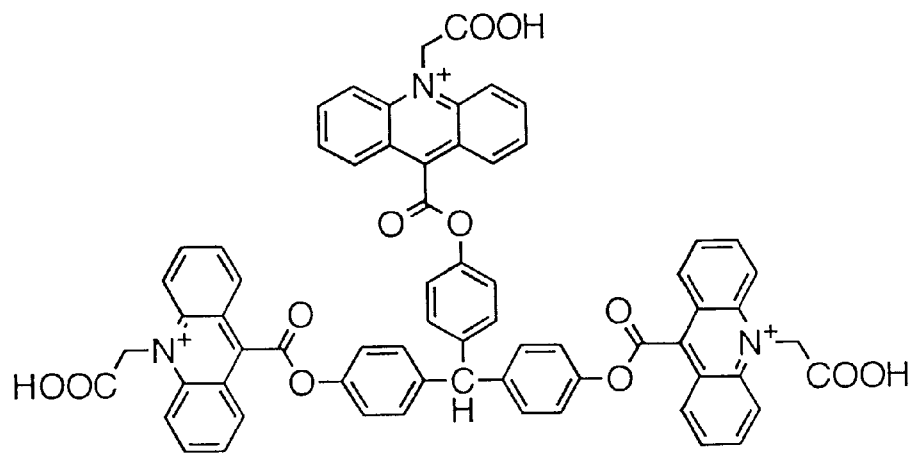
Figure 7:
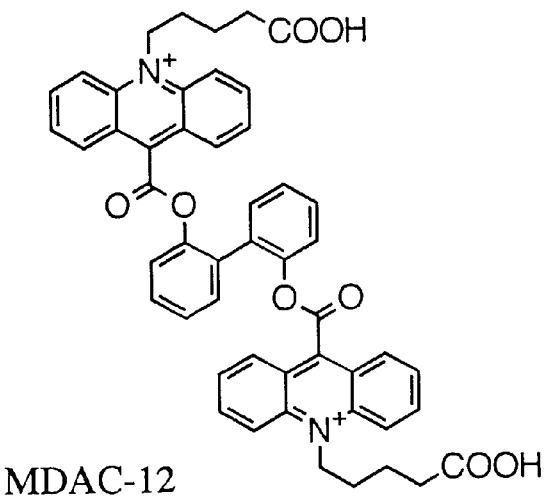
FIG. 7 shows chemical formulae of the acridinium compounds of the present invention synthesized in Examples 12 to 14.
Figure 7:
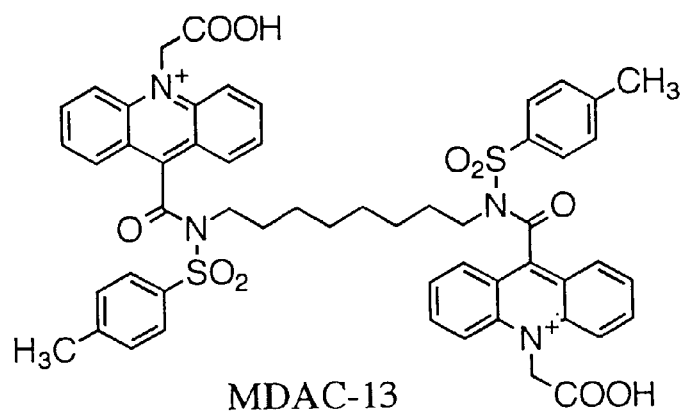
Figure 7:
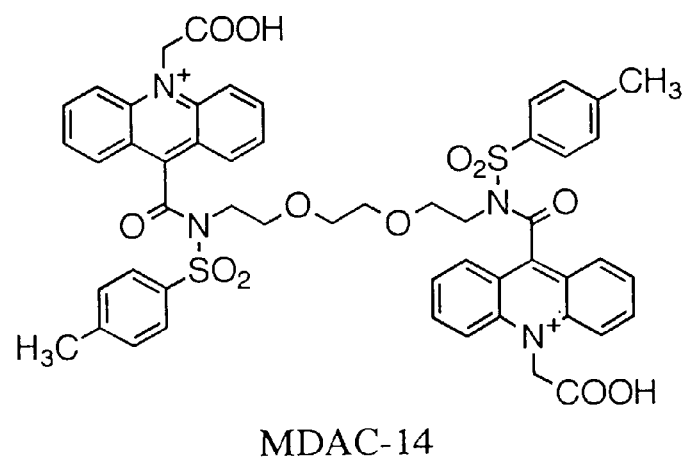
Figure 8:
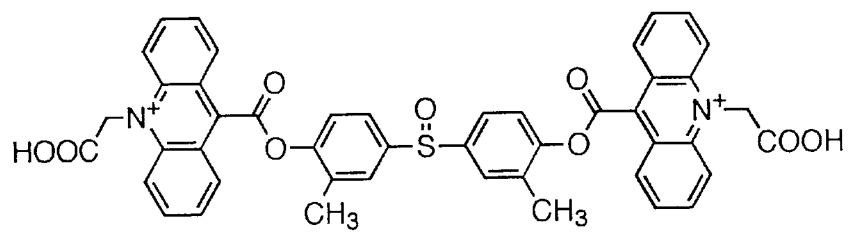
FIG. 8 shows chemical formulae of the acridinium compounds of the present invention synthesized in Examples 15 to 18.
Figure 8:
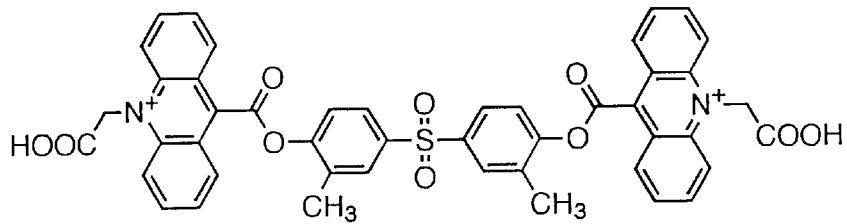
Figure 8:
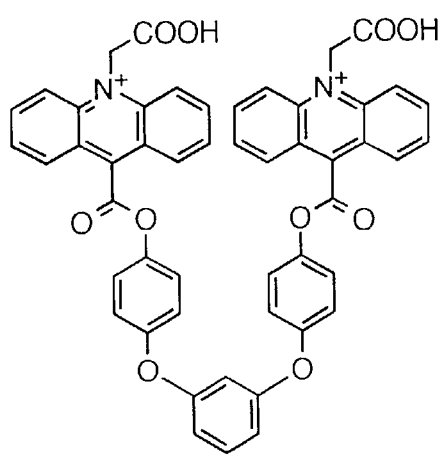
Figure 8:
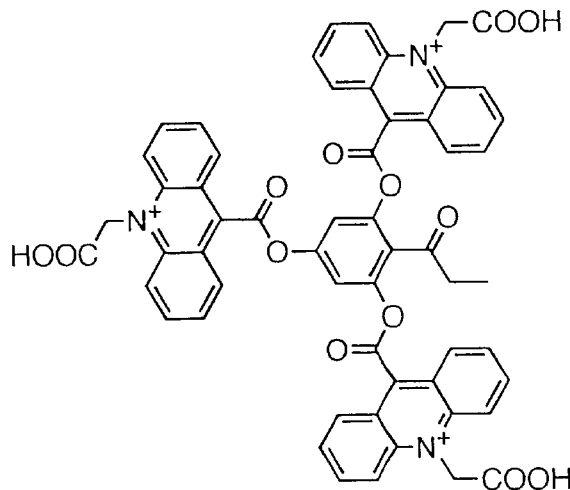
Figure 9:
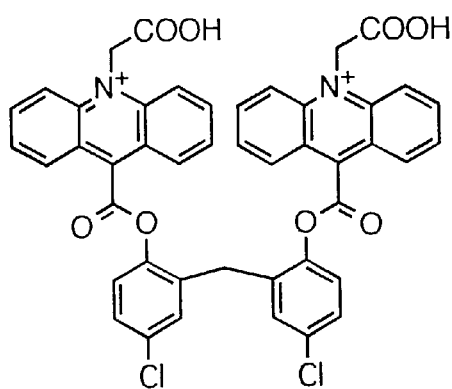
FIG. 9 shows chemical formulae of the acridinium compounds of the present invention synthesized in Examples 19 to 22.
Figure 9:
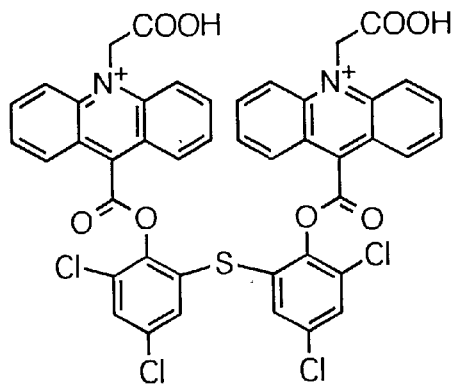
Figure 9:
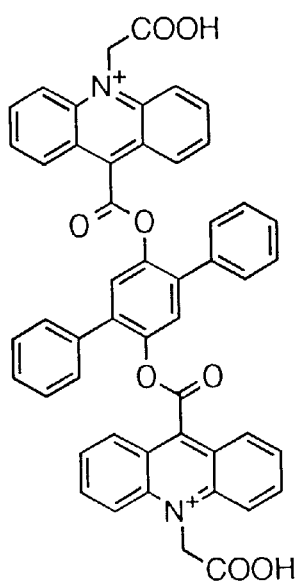
Figure 9:
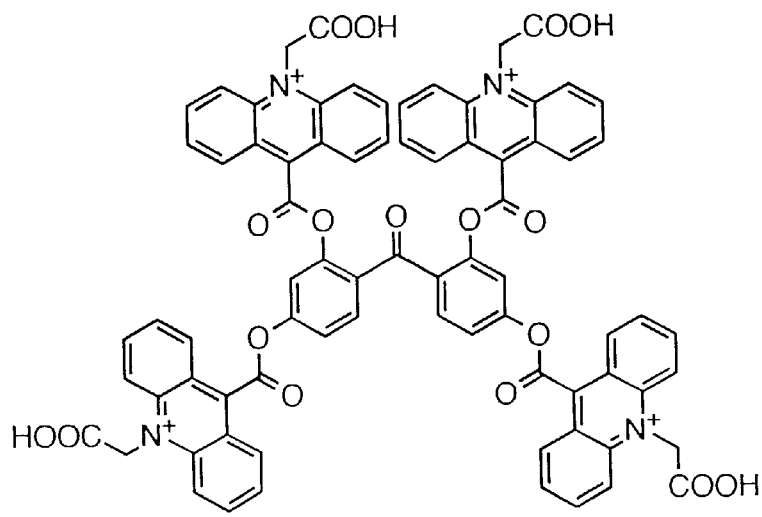
Figure 10:
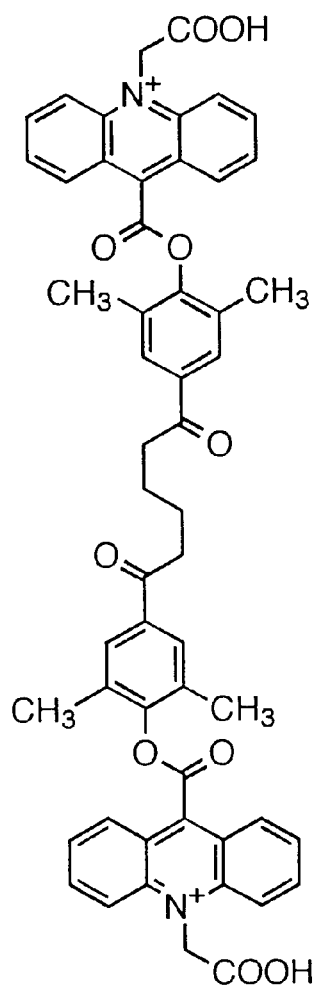
FIG. 10 shows chemical formulae of the acridinium compounds of the present invention synthesized in Examples 23 and 24.
Figure 10:
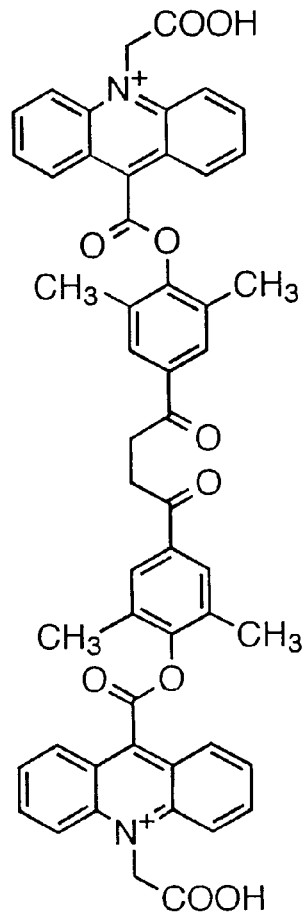
Figure 11:
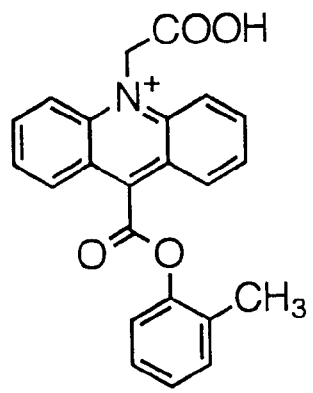
FIG. 11 shows chemical formulae of the acridinium compounds of the prior art synthesized in Comparative Examples.
Figure 11:
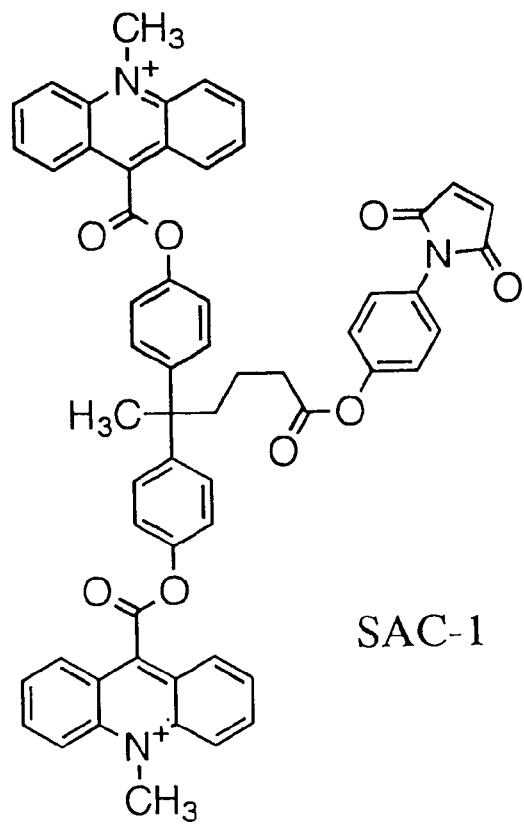

The results are shown in FIG. 3. As demonstrated in FIG. 3, the residual luminescence activity was 80% in the case of MDAC-1 in contrast to the case of SAC-1 wherein the residual activity was 16%.

Example 27

A $3.4\times 10^{-3}$M DMF solution for each of MDAC-8 produced in Example 8 and MAC-1 produced in Comparative Example 1 were prepared. To 80 µl of the MDAC-8 solution were added 20 µl of $7.2\times 10^{-2}$M DMF solution of N-hydroxysuccinimide (NHS) (manufactured by WAKO Junyaku Kogyo K. K.), and 20 µl of $5.4\times 10^{-2}$M DMF/water (4/6) mixed solution of 1-ethyl-3-(3-dimethylaminopropyl)carbodiimide hydrochloride (WSC) (Dojin Kagaku K. K.) in an ice bath; and to the MAC-1 were added 20 µl of $3.6\times 10^{-2}$M DMF solution of NHS and 20 µl of $2.7\times 10^{-2}$M DMF/water (4/6) mixed solution of WSC in an ice bath, and the resulting mixtures were respectively allowed to react at room temperature for 3 hours. Next, 7 µl of the reaction mixture was added to 70 µl of bovine serum albumin (BSA) (manufactured by Seikagaku Kogyo K. K.) solution adjusted to 3 mg/ml with 0.1M sodium carbonate buffer, pH 9.5. After stirring at room temperature for 60 minutes, the reaction mixture was applied to Sephadex G-25 column (Pharmacia) and eluted with 5 mM PB, pH 8.0 to prepare acridinium ester-labeled BSA. Next, luminescence and protein quantity were measured for the thus prepared acridinium-ester labeled BSA. The acridinium ester-labeled BSA had a luminescence per 1 mole protein of $5.9\times 10^{21}$ counts/mol in the case of MDAC-8 and $1.8\times 10^{21}$ in the case of mAC-1, indicating higher reaction rate per mole of the MDAC-8.

Example 28

(1) Preparation of acridinium-ester labeled antibody

A $0.75\times 10^{-3}$M DMF solution of MDAC-1 produced in Example 1 was prepared, and 20 µl of $1.6\times 10^{-2}$M DMF solution of NHS and 20 µl of $1.2\times 10^{-2}$M DMF/water (4/6) mixed solution of WSC in an ice bath were added to 80 µl of MDAC-1 solution. The resulting mixture was allowed to react at room temperature for 3 hours. Next, 7 µl of the reaction mixture was added to 70 µl of anti-hCGα subunit monoclonal antibody (Mochida Pharmaceutical) solution adjusted to 3 mg/ml with 0.1M sodium carbonate buffer, pH 9.0. After stirring at room temperature for 60 minutes, the reaction mixture was added to Sephadex G-25 column (Pharmacia) and eluted with 5 mM PB, pH 8.0 to prepare acridinium ester-labeled monoclonal antibody.

Next, the acridinium ester-labeled monoclonal antibody was purified by applying the labeled antibody to anion exchange column having diethylaminoethyl (DEAE) Sepharose (Whatmann) charged therein and eluting the labeled antibody, by salt concentration gradient of 5 mM phosphate buffer solution, pH 8.0. The resulting labeled monoclonal antibody was then measured for its luminescence and protein quantity. Calculation of the ratio of the acridinium ester concentration (determined from the luminescence) to the protein (antibody) concentration revealed that one molecule of the antibody is labeled with about 1 molecule of MDAC-1.

(2) Preparation of acridinium-ester labeled DNA probe

A $3.0 \times 10^{-2}$M DMF solution of MDAC-1 produced in Example 1 was prepared, and to 40 μl of this solution were added 10 μl of 0.24M DMF solution of NHS, and 10 μl of 0.18M DMF/water (4/6) mixed solution of WSC in an ice bath, and the resulting mixture was allowed to react at room temperature for 3 hours. Next, 8 μl of the reaction mixture was added to 20 μl of oligomer probe [HBVC region 1941–1970, 30 mer (HB1010—NH$_2$ (3'), synthesized with a nucleic acid synthesizer] solution adjusted to 0.15 mg/ml with 0.1M sodium carbonate buffer, pH 9.0. After stirring at room temperature for 30 minutes, the reaction solution was applied to Sephadex G-25 column (Pharmacia) and eluted with 20 mM acetate buffer, pH 5.5-acetonitrile (8:2) to prepare labeled HB1010.

The thus prepared labeled HB1010 was eluted by reverse phase HPLC with a concentration gradient of triethylamine-acetate/water-acetonitrile. The fractions were respectively evaluated for their absorption at 260 nm n luminescence, and the fractions exhibiting both absorption and luminescence were collected. The thus collected fractions were desalted by ethanol precipitation, and to this solution was added 50 μl of assay buffer [4×SSC (1×SSC=0.15M NaCl, 0.015M sodium citrate), 1× Denhard's (0.02% polyvinyl pyrrolidone, 0.02% ficoll, 0.02% BSA), 0.2 mg/ml modified salmon sperm DNA, 0.2% SDS] for dissolution to thereby prepare an acridinium-ester labeled DNA probe.

(3) Chemiluminescence immunoassay using the acridinium-ester labeled antibody

To polystylene tubes having immobilized therewith 2 μg of anti-hCGβ subunit monoclonal antibody (Mochida Pharmaceutical) were respectively added 150 μl of assay buffer [10% normal rabbit serum (Pelfreeze Inc.), 1% mouse serum (Jikken Dobutsu Kyokai), 0.1% BSA/PBS] and 50 μl of hCG standards (1st. IRP 75/537) of various concentrations, and the tubes were shaken at room temperature for one hour. After washing the tube with washing solution (physiological saline containing 0.005% Tween 20) for three times, 200 μl of the solution prepared by diluting the acridinium-ester labeled anti-hCG monoclonal antibody prepared in the above (1) with the assay buffer was added to the tube, and the tube was shaken at room temperature for one hour. The tube was washed with the washing solution for three times, and to the tube was added 300 μl of 0.5% hydrogen peroxide/0.1N nitric acid solution, and then, 300 μl of 0.125% cetyltrimethylammonium chloride/0.25N sodium hydroxide solution. The resulting chemiluminescence was measured for 2 seconds with a chemiluminescence measuring apparatus, AutoLumat LB953 (Berthold, FRG). The thus depicted standard curve is shown in FIG. 1. The limit of hCG detection in this standard curve was 0.01 IU/L.

(4) Assay of HBV-DNA using the acridinium-ester labeled DNA probe

Figure 2:
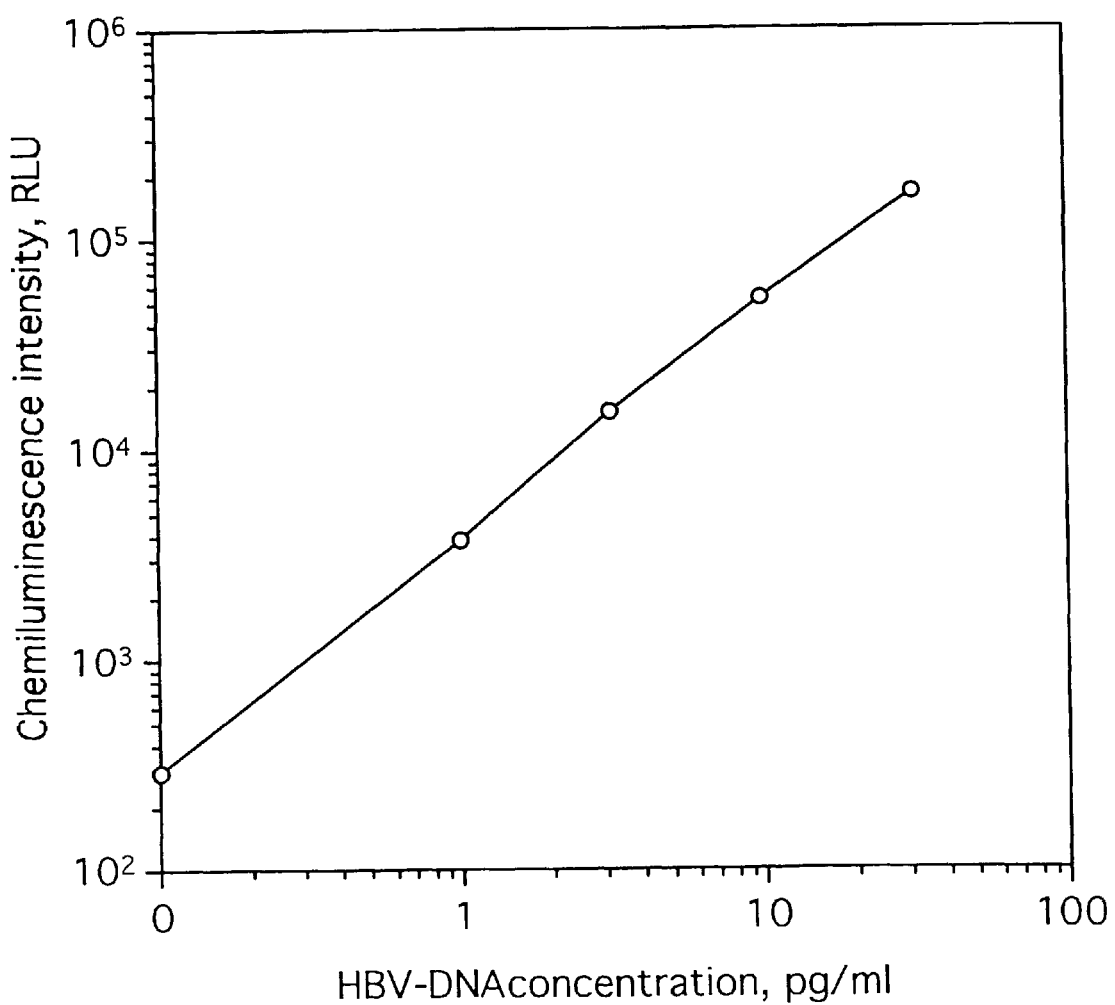
FIG. 2 is a graph showing the standard curve depicted by measuring chemiluminescence intensity in relation to HBV-DNA concentration.

A 3.2 kb sequence was cut out with restriction enzyme BamHI from pBRHBadr4 vector having HBV-DNA (3.2 kb) sequence cloned therein, and the cut out sequence was separated and purified by agarose electrophoresis. The resulting HBV-DNA was evaluated for its concentration by measuring absorption at 260 nm, and diluted with 0.01M Tris-HCl buffer, pH 8.0 containing 0.001M EDTA to prepare standard solutions ranging from 0.1 to 100 pg/ml. The standard solutions were thermally denatured by treating at 100° C. for 10 minutes, and dispensed in the wells of 96 well microtiter plate for immobilization by adsorption. After rinsing the wells, 200 μl of assay buffer was dispensed in each well, and preincubated at 60° C. for one hour. To the well was then dispensed $1 \times 10^7$ counts/well of the acridinium ester-labeled DNA probe solution prepared in the above (2), and the reaction (hybridization) was allowed to take place at 60° C. for one hour. After removing the supernatant from the reaction solution, 0.2×SSC and 0.2% SDS at 50° C. were added and the plate was incubated for 5 minutes (for washing). The procedure was repeated 5 times. The microtiter plate was thereafter placed in a chemiluminescence measuring apparatus, AutoLumat LB953 (Berthold, FRG), and 100 μl of 0.5% hydrogen peroxide/0.1N nitric acid solution, and then, 100 μl of 0.125% cetyltrimethylammonium chloride/0.25N sodium hydroxide solution were added to the well, and the resulting chemiluminescence was measured for 2 seconds. The thus depicted standard curve is shown in FIG. 2. The limit of HBV-DNA detection in this standard curve was 0.1 pg/ml.

(5) Stability of the acridinium-labeled antibody

The acridinium ester-labeled antibody prepared in the above (1) was diluted with assay buffer to the antibody concentration of 0.1 μg/ml, and the thus diluted solution was stored at a temperature of 45° C. and a humidity of 90% for 7 days. The thus stored acridinium ester-labeled antibody was aliquoted at appropriate time intervals, and evaluated for the luminescence in accordance with the above (3). No decrease in the chemical luminescence of the labeled substance was found.

(6) Stability of the acridinium ester-labeled DNA probe

The acridinium ester-labeled DNA probe prepared in the above (2) was diluted with assay buffer to produce a solution of 50 ng/ml. The probe prepared with this solution was evaluated for the stability under hybridization conditions (60° C., treatment for one hour). No decrease in the luminescence activity was observed.

EFFECTS OF THE INVENTION

The novel acridinium compound of the present invention is useful as a chemiluminescent substance for labeling a specific binding substance. The compound exhibits a high chemiluminescence yield as well as high stability.

What is claimed is:

1. A chemiluminescent compound represented by formula (I):

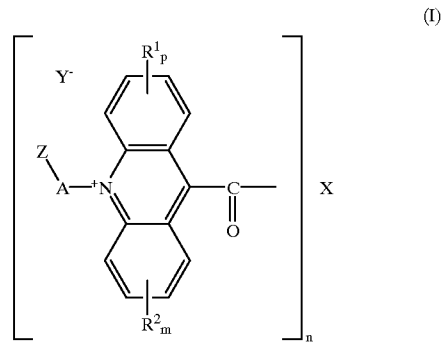

wherein A is a linker selected from a $C_{1-4}$ alkylene group which may optionally have at least one substituent; Z is a binding group selected from the group consisting of a carboxyl group, a cyano group, an isocyanate group, an isothiocyanate group, an azide group, a sulfonyl group, a halosulfonyl group, a halogenated carbonyl group, an N-succinimidyloxycarbonyl group, an N-phthalimidyloxycarbonyl group, and a maleimidyl group; Y is a counter ion; $R^1$ and $R^2$ are independently a methyl, ethyl, methoxy, ethoxy, chlorine, bromine or fluorine; p and m are independently an integer of from 0 to 4; n is an integer of from 2 to 5; and X is an organic intervening moiety with a valence of n, having a phenyloxy group and X binds to a carbonyl carbon bonded to the 9-position of the acridinium ring through the oxygen of the phenyloxy group, wherein said phenyloxy group is substituted at its ortho position with an alkyl group, an aryl group or an alkoxy group and if a plurality of phenyloxy groups is present, the plurality of phenyloxy groups are mutually bound with a directly bound alkyl group, carbonyl group, sulfonyl group, sulfinyl group or aryl group; and which exhibits i) a luminescence of at least $2.4 \times 10^{20}$ counts/mol, and ii) residual luminescence activity of at least 50% of the original luminescence when the compound is stored in a buffer of pH 8.0 at 45° C. for one week in the dark.

2. A chemiluminescent compound, represented by formula (I):

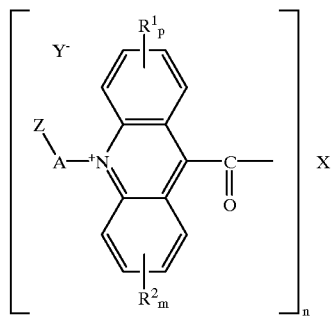

wherein A is a linker selected from $C_{1-4}$ alkylene group; Z is a binding group selected from the group consisting of a carboxyl group, a cyano group, an isocyanate group, an isothiocyanate group, an azide group, a sulfonyl group, a halosulfonyl group, a halogenated carbonyl group, an N-succinimidyloxycarbonyl group, an N-phthalimidyloxycarbonyl group, and a maleimidyl group; Y is a counter ion; $R^1$ and $R^2$ are independently a methyl, ethyl, methoxy, ethoxy, chlorine, bromine or fluorine; p and m are independently an integer of from 0 to 4; n is an integer of from 2 to 5; and X is an organic intervening moiety with a valence of n, having a phenyloxy group and X binds to a carbonyl carbon bonded to the 9-position of the acridinium ring through the oxygen of the phenyloxy group, wherein said phenyloxy group is substituted at its ortho position with an alkyl group, an aryl group or an alkoxy group and if a plurality of phenyloxy groups is present, the plurality of phenyloxy groups are mutually bound with a directly bound alkyl group, carbonyl group, sulfonyl group, sulfinyl group or aryl group; and which exhibits i) a luminescence of at least $2.4 \times 10^{20}$ counts/mol, and ii) residual luminescence activity of at least 50% of the original luminescence when the compound is stored in a buffer of pH 8.0 at 45° C. for one week in the dark.

3. A chemiluminescent compound according to claim 1, wherein A is a $C_{1-4}$ alkylene group, Z is a carboxyl group, p and m are 0; n is 2 and X is selected from the group represented by the following formula:

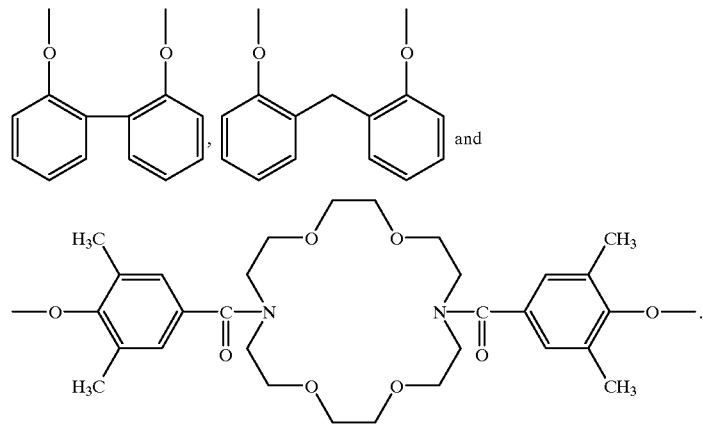

4. A chemiluminescent compound according to claim 1, wherein the compound represented by said formula (I) is selected from the group consisting of the following formulae:

2'-[2"-(10'"-carboxymethylacridinium-9'"-ylcarbonyloxy)phenyl)phenyl 10-carboxymethylacridinium-9-carboxylate 2Y⁻, 4'-({1", 10"-diaza-10"-[(4'"-[10""-carboxymethylacridinium-9""-ylcarbonyloxy]-3'",5'"-dimethylphenyl)carbonyl]-4",7", 13",16"-tetraoxacyclooctadecyl}carbonyl)-2', 6'-dimethylphenyl 10-carboxymethylacridinium-9-carboxylate 2Y⁻, 2'-({[2"-10'"-carboxymethylacridinium-9'"-ylcarbonyloxy)phenyl]methyl}phenyl 10-carboxymethylacridinium-9-carboxylate 2Y⁻, 2'-[2"-(10'"-carboxymethyl-2'", 7'"-dimethoxyacridinium-9'"-ylcarbonyloxy)phenyl] phenyl 10-carboxymethyl-2,7-dimethoxyacridinium-9-carboxylate 2Y⁻, 2'-{2"-[10'"-(4-carboxybutyl)acridinium-9'"-ylcarbonyloxy]phenyl}phenyl 10-(4-carboxybutyl)acridinium-9-carboxyiate 2Y⁻, 4'-{6"-[4'"-(10""-carboxymethylacridinium-9""-ylcarbonyloxy)-3'",5'"-dimethylphenyl]6"-oxohexanoyl}-2',6'-dimethylphenyl 10-carboxymethylacridinium-9-carboxylate 2Y⁻, and 4'-{6"-[4'"-(10""-carboxymethylacridinium-9""-ylcarbonyloxy)-3'",5'"-dimethylphenyl]-4"-oxobutanoyl}-2',6'-dimethylphenyl 10-carboxymethylacridinium-9-carboxylate 2Y⁻, wherein 2Y⁻ represents counter ions.

5. The chemiluminescent compound according to claim 1 wherein said counter ion is selected from the group consisting of $CH_3SO_4^-$, $FSO_3^-$, $CF_3SO_3^-$, $C_4F_9SO_3^-$, $CF_3COO^-$, a halide ion, $BF_4^-$, $PF4^-$, and a counter ion of the following formula

6. The chemiluminescent compound according to claim 2 wherein said counter ion is selected from the group consisting of $CH_3SO_4^-$, $FSO_3^-$, $CF_3SO_3^-$, $C_4F_9SO_3^-$, $CF_3COO^-$, a halide ion, $BF_4^-$, $PF_4^-$, and a counter ion of the following formula

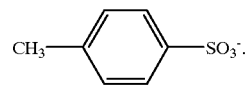

7. The chemiluminescent compound according to claim 3 wherein said counter ion is selected from the group consisting of $CH_3SO_4^-$, $FSO_3^-$, $CF_3SO_3^-$, $C_4F_9SO_3^-$, $CF_3COO^-$, a halide ion, $BF_4^-$, $PF_4^-$, and a counter ion of the following formula

8. The chemiluminescent compound according to claim 4 wherein said counter ion is selected from the group consisting of $CH_3SO_4^-$, $FSO_3^-$, $CF_3SO_3^-$, $C_4F_9SO_3^-$, $CF_3COO^-$, a halide ion, $BF_4^-$, $PF_4^-$, and a counter ion of the following formula

* * * * *